(12) United States Patent
Cherkaoui et al.

(10) Patent No.: US 7,687,118 B2
(45) Date of Patent: Mar. 30, 2010

(54) PHOTOCROSSLINKABLE MATERIALS

(75) Inventors: Zoubair Mohammed Cherkaoui, Allschwil (CH); Thomas Bachels, Grenzach-Wyhlen (DE); Guy Marck, Schlierbach (FR); Olivier Müller, Lautenbach (FR); Andreas Schuster, Freiburg (DE); Hubert Seiberle, Weil am Rhein (DE)

(73) Assignee: Rolic AG, Zug (CH)

( * ) Notice: Subject to any disclaimer, the term of this patent is extended or adjusted under 35 U.S.C. 154(b) by 363 days.

(21) Appl. No.: 11/665,351

(22) PCT Filed: Oct. 5, 2005

(86) PCT No.: PCT/CH2005/000577

§ 371 (c)(1),
(2), (4) Date: Apr. 13, 2007

(87) PCT Pub. No.: WO2006/039824

PCT Pub. Date: Apr. 20, 2006

(65) Prior Publication Data

US 2008/0069968 A1    Mar. 20, 2008

(30) Foreign Application Priority Data

Oct. 13, 2004    (EP) .................................. 04405643

(51) Int. Cl.
C09K 19/00    (2006.01)
C09K 19/38    (2006.01)
C08F 2/46     (2006.01)
C08J 3/28     (2006.01)

(52) U.S. Cl. .................. 428/1.26; 428/1.27; 430/287.1; 430/20; 349/135; 349/183; 349/193; 528/345; 528/335; 522/149; 522/164

(58) Field of Classification Search ................ 428/1.26, 428/1.27; 430/287.1; 349/135; 528/345
See application file for complete search history.

(56) References Cited

U.S. PATENT DOCUMENTS

| 5,833,880 | A |    | 11/1998 | Siemensmeyer et al. |
|---|---|---|---|---|
| 6,027,772 | A |    | 2/2000 | Han |
| 6,066,696 | A |    | 5/2000 | Yu et al. |
| 6,303,742 | B1 |    | 10/2001 | Okada et al. |
| 6,340,506 | B1 |    | 1/2002 | Buchecker et al. |
| 6,608,661 | B1 | * | 8/2003 | Schadt et al. ................ 349/124 |
| 6,831,148 | B2 | * | 12/2004 | Buchecker et al. ........... 528/310 |
| 2004/0158050 | A1 | * | 8/2004 | Lee et al. ..................... 534/751 |

FOREIGN PATENT DOCUMENTS

| EP | 1 277 770 A1 | 1/2003 |
|---|---|---|
| EP | 1 386 910 A1 | 2/2004 |
| EP | 1 261 659 B1 | 10/2004 |
| JP | 10-195296 A | 7/1998 |
| JP | 10-232400 A | 9/1998 |
| WO | WO 99/15576 A1 | 4/1999 |
| WO | WO 99/49360 A1 | 9/1999 |
| WO | WO 99/51676 A1 | 10/1999 |

OTHER PUBLICATIONS

J.M. Guglieiminetti, et al, "Chiral α Substituted Acrylates Side-Chain Polymers With a Cinnamate Core", Polymer Bulletin, vol. 16, 1986, pp. 411-418.
M. Schadt et al., Jpn. J. Appl. Phys., vol. 31 (1992) pp. 2155-2164.
K. Schmitt et al., Proceedings of EuroDisplay 99, Sep. 6-9, 1999, pp. 437-440.

* cited by examiner

*Primary Examiner*—Randy Gulakowski
*Assistant Examiner*—Rachel Kahn
(74) *Attorney, Agent, or Firm*—Sughrue Mion, PLLC

(57) ABSTRACT

A diamine compound is proposed as well as polymers, copolymers, polyamic acids, polyamic acid esters, or polyimides based on such compound. The compound is represented by one of the general formulae (Ia) and (Ib). It could be shown that such structures, in particular for a specific choice of the residue B, provide, if e.g. used as orientation layers, a photostable, vertically aligning material with an improved VHR.

46 Claims, No Drawings

PHOTOCROSSLINKABLE MATERIALS

TECHNICAL FIELD

The invention relates to diamine compounds, represented by the general formulae (Ia) and (Ib), and also relates to oligomers and polymers from the class of polyamic acids, polyamic acid esters or polyimides (and any mixtures thereof) obtained by the reaction of a diamine compound represented by the general formulae (Ia) and (Ib) and optionally of one or more additional other diamines, with one or more tetracarboxylic acid anhydrides, and to the use of these diamine compounds, oligomers and polymers for the preparation of orientation layers for liquid crystals and in the construction of unstructured and structured optical elements and multi-layer systems.

BACKGROUND OF THE INVENTION

Liquid crystal displays (LCDs) are becoming increasingly dominant in advanced visualization devices. LCDs offer favourable characteristics with respect to image quality (high luminance, high resolution, colour and grey scale capability), power consumption as well as dimensions and weight (flat panel displays). The use of commercial LCDs has become widespread, e.g. in automotive and telecommunication instruments, as well as in monitors of notebooks, desktop computers, television sets, etc. Today the need for LCDs in television applications is rapidly growing. Recently developed LCD modes possess high potentials in achieving fast response times, wide viewing angles and high luminance. Amongst other newly developed LCD modes, the MVA (multi-domain vertical alignment) mode appears to be the most promising for the use in modern television applications.

In the MVA mode the liquid crystal molecules are usually nearly vertically aligned with respect to the surface of the substrates. By using protrusions (or other alignment subdivisions) on the surface of the substrate, the liquid crystal molecules become locally pre-tilted within a single cell in more than one direction, leading to domains switchable in different directions. This multi-domain configuration exhibits very good display performance, with wide viewing angles of up to 160° in any direction, short response times (below 20 ms), high contrast ratios (up to 700:1) and high brightness.

However, by means of using protrusions only, it is difficult to clearly define the domain space within a single pixel. Therefore the MVA mode demands additional manufacturing steps to ensure shape effects as well as electrical field effects on both the upper and lower substrate; hence all in all leading to complex manufacturing procedures.

In order to by-pass this technical challenge, the availability of an alignment layer would be desirable, which directly leads to pre-defined alignment directions within each pixel domain and having well controllable off-axis angles with respect to the normal axis of the substrate.

Methods for the preparation of orientation layers for liquid crystal materials are well known to the skilled person. Customarily used uniaxially rubbed polymer orientation layers, such as for example polyimides, however, do have a series of disadvantages, like the formation and deposition of dust during the rubbing process and concomitant partial destruction of the thin film transistors.

Scratches due to brushing is another issue associated with this technique, which is particularly evident when the pixels are of the order of 10 microns or even lower, like e.g. in micro-display applications. Because of the strong optical magnification, which is required to visualize the displayed information, scratches easily become visible and are also the cause for the reduction of the contrast level. Furthermore, the rubbing process does not allow the production of structured layers.

The production procedure for obtaining orientation layers in which the direction of orientation is induced by irradiation with polarized light is not faced with the problems inherent to the rubbing process. With the irradiation technique it is furthermore also possible to create areas having different orientation and thus to structure the orientation layer as described for example in Jpn. J. Appl. Phys., 31 (1992), 215-564 (Schadt et al).

Using the linearly photo-polymerizable alignment (LPP) technique, the possibility of realizing a four-domain vertical aligned nematic (VAN) LCD was demonstrated some years ago (K. Schmitt, M. Schadt; Proceedings of EuroDisplay 99, 6-9 Sep., 1999). The four-domain VAN-LCD exhibits an excellent off-state angular brightness performance.

Apart from the current display performance requirements to be fulfilled in modern TV applications, the use of appropriate LPP materials is furthermore also guided by the necessity to achieve specific optical and electro-optical properties, e.g. with respect to the compatibility with the TFT (thin film transistors). Other important characteristics of the materials must also be taken into consideration, i.e. those crucial parameters directly related to and dependent on the molecular properties of the material. Primarily such characteristics are:

High voltage holding ratio (VHR), i.e. VHR of >90% (measured at 80° C.)

High stability of the induced pre-tilt angle against light and heat

Low alignment energy profile (short irradiation time and/or low irradiation energy)

In the case of LCDs of thin-film transistor type a certain amount of charge is applied over the course of a very short period of time to the electrodes of a pixel and must not subsequently drain away by means of the resistance of the liquid crystal. The ability to hold that charge and thus to hold the voltage drop over the liquid crystal is quantified by what is known as the "voltage holding ratio" (VHR). It is the ratio of the RMS-voltage (root mean square voltage) at a pixel within one frame period and the initial value of the voltage applied.

Photo-reactive materials for orientation layers with improved voltage holding ratios (VHR) are described in WO-A-99/49360, JP-A-10-195296 corresponding to U.S. Pat. No. 6,066,696, JP-A-10-232400 corresponding to U.S. Pat. No. 6,027,772, WO-A-99/15576 and WO-A-99/51662. In WO-A-99/49360, JP-A-10-195296 and JP-A-10-232400 blends of polymeric compounds are described, containing photo-reactive polymers and polyimides.

In WO-A-99/15576 and WO-A-99/51662 polyimides having photo-reactive cinnamate groups incorporated in their side chains are described. WO-A-99/15576 for instance discloses photo-active polymers which contain as side-chain specific photo-cross-linkable groups and of which a typical monomer unit is 6-{2-methoxy-4-[(1E)-3-methoxy-3-oxo-prop-1-enyl]phenoxy}hexyl 3,5-diaminobenzoate.

SUMMARY OF THE INVENTION

In the above cited references it was generally demonstrated that in order to achieve the aforementioned important parameters, molecular structures combining firstly a polyamic/polyimide backbone (i.e. delivering molecular polarity) and secondly side chains with an incorporated photo-reactive group, such as a cinnamic acid residue, are suitable for the general concept of planar orientation [requiring only slight pretilt angles, like e.g. being used in TN (twisted nematic) devices]. However, these types of molecular structures, primarily developed for TN applications, cannot directly be utilized in MVA applications. From the comparative examples provided below, it can be seen that when molecular structures, providing high voltage holding ratios in the TN mode, are slightly modified in order to induce vertical alignment, for example simply by increasing the length of a peripheral alkyl chain, a strong drop of the VHR value is observed. This indicates that in case of the MVA mode not only the molecular polarity (being sufficient in case of the TN mode) has to be taken into consideration, but also other molecular parameters. It has surprisingly been found, that in addition to the molecular polarity, also the molecular architecture of the LPP material as such plays a predominant role in obtaining MVA materials having optimised properties, such as the required high voltage holding ratios, the adjustable pre-tilt angles required for the MVA mode and their stability to light and heat.

Thus, a first preferred embodiment of the present invention relates to diamine compounds represented by one of the general formulae (Ia) and (Ib) and to alignment layers/materials comprising these diamine compounds:

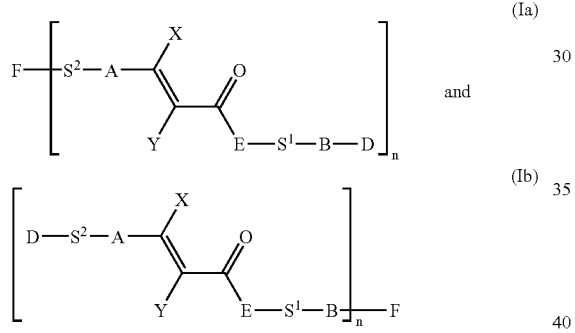

wherein:

A, B each independently represents a carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms. Examples of such carbocyclic or heterocyclic aromatic groups include but are not limited to: pyrimidine-diyl, pyridine-diyl, thiophenylene, furanylene, phenanthrylene, naphthylene, biphenylene or phenylene. The carbocyclic or heterocyclic aromatic groups can be unsubstituted or mono- or poly-substituted by a halogen atom, by a hydroxy group and/or by a polar group like a nitro, cyano or a carboxy group, and/or by a cyclic, straight-chain or branched alkyl residue having from 1 to 30 carbon atoms, which is unsubstituted, mono- or poly-substituted by methyl, fluorine and/or chlorine, wherein one or more, preferably non-adjacent, —$CH_2$— group may independently be replaced by a group selected from —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, and —Si($CH_3$)$_2$—O—Si($CH_3$)$_2$—, an aromatic or an alicyclic group, and wherein:

$R^1$ represents a hydrogen atom or lower alkyl;
with the proviso that oxygen atoms are not directly linked to each other.

The carbocyclic or heterocyclic aromatic groups can also be independently substituted by an acryloyloxy, alkoxy, alkylcarbonyloxy, alkyloxycarbonyloxy, alkyloxocarbonyloxy methacryloyloxy, vinyl, vinyloxy and/or allyloxy group, having from 1 to 20 carbon atoms, preferably having from 1 to 10 carbon atoms.

B in particular is preferably chosen from 1,4-phenylene, 4,4'-biphenylene, 2,7-phenanthrylene or 2,7- or 2,6-naphthalene, which may be substituted as outlined above. It is preferred that the unit B, e.g. by means of the linking points to adjacent groups $S^1$ and D/F, provides an extended, quasi-linear form, and a long molecular axis.

D represents a hydrogen atom, a halogen atom, a polar group like nitro, cyano or carboxy, —$CF_3$, a silane group, a siloxane group, or a cyclic, straight-chain or branched alkyl residue having from 1 to 40 carbon atoms, which is unsubstituted, mono-substituted by cyano, fluorine or chlorine, or poly-substituted by fluorine and/or chlorine, or substituted by a polymerizable group such as $CH_2$=CH—, $CH_2$=C($CH_3$)—, $CH_2$=CH—(CO)O—, $CH_2$=CH—O—, $CH_2$=C($CH_3$)—(CO)O—, $CH_2$=C($CH_3$)—O—, and wherein one or more preferably non-adjacent —$CH_2$— groups may independently be replaced by a group preferably selected from —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, or —Si($CH_3$)$_2$—O—Si($CH_3$)$_2$—, wherein $R^1$ represents a hydrogen atom or lower alkyl.

E represents an oxygen atom, a sulphur atom, —C($R^2$)$R^3$— or —$NR^4$—, wherein:

$R^2$ or $R^3$ is hydrogen or a cyclic, straight-chain or branched alkyl residue which is unsubstituted, mono-substituted by cyano, fluorine or chlorine, or poly-substituted by fluorine and/or chlorine, having from 1 to 24 carbon atoms, wherein one or more non-adjacent —$CH_2$— groups may independently be replaced by a group preferably selected from —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, —Si($CH_3$)$_2$— and —Si($CH_3$)$_2$—O—Si($CH_3$)$_2$—, wherein:

$R^1$ represents a hydrogen atom or lower alkyl;
with the proviso that at least one of $R^2$ and $R^3$ is not hydrogen; and $R^4$ represents a hydrogen atom or lower alkyl.

$S^1$, $S^2$ each independently represents a single bond or a spacer unit such as a straight-chain or branched alkylene group which is unsubstituted, mono or poly-substituted by a cyano group and/or by halogen atoms, having from 1 to 24 carbon atoms, wherein one or more —$CH_2$— groups may independently be replaced by a group represented by the general formula (II):

wherein:

$C^1$, $C^2$ each independently represents a non-aromatic, aromatic, optionally substituted carbocyclic or heterocyclic group, preferably connected to each other at the opposite positions via the bridging groups $Z^1$ and $Z^2$, so that groups $S^1$ and/or $S^2$ have a long molecular axis, and $Z^1$, $Z^2$ each independently represents a bridging group preferably selected from —CH(OH)—, —O—, —CO—, —CH$_2$(CO)—, —SO—, —CH$_2$(SO)—, —SO$_2$—, —CH$_2$(SO$_2$)—, —COO—, —OCO—, —COCF$_2$—, —CF$_2$CO—, —S—CO—, —CO—S—, —SOO—, —OSO—, —SOS—, —CH$_2$—CH$_2$—, —OCH$_2$—, —CH$_2$O—, —CH=CH—, —C≡C—, —CH=CH—COO—, —OCO—CH=CH—, —CH=N—, —C(CH$_3$)=N—, —O—CO—O— N=N— or a single bond; and $a^1$, $a^2$ each independently represents an integer from 0 to 3, such that $a^1 + a^2 \leq 4$.

F represents an optionally substituted aliphatic, aromatic or alicyclic diamino group having from 1 to 40 carbon atoms, preferably selected from formula (III):

HN(R$^5$)-(Sp$^1$)$_{k1}$-(X$^1$)$_{t1}$-(Z$^3$-C$^3$)$_{a3}$-(Z$^4$-C$^4$)$_{a4}$—(X$^2$)$_{t2}$-(Sp$^2$)$_{k2}$-N(R$^6$)H wherein:

Sp$^1$, Sp$^2$ each independently represents an optionally substituted straight-chain or branched alkylene group having from 1 to 20 carbon atoms, in which one or more, preferably non-adjacent, C-atoms may be replaced by a heteroatom, and wherein it is optionally possible that one or more carbon-carbon single bonds are replaced by a carbon-carbon double or by a carbon-carbon triple bond; and R$^5$, R$^6$ each independently represents a hydrogen atom or lower alkyl; and k$^1$, k$^2$ each independently is an integer having a value of 0 or 1; and X$^1$, X$^2$ each independently represents a linking group, preferably selected from —O—, —S—, —NH—, —N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —CH$_2$—CH$_2$—, —OCH$_2$—, —CH$_2$O—, —CH=CH—, or —C≡C— or a single bond; and t$^1$, t$^2$ each independently is an integer having a value of 0 or 1; and C$^3$, C$^4$ each independently represents a non-aromatic, aromatic, optionally substituted carbocyclic or heterocyclic group, preferably connected to each other at opposite positions via the bridging groups Z$^3$ and Z$^4$; so that they contribute to the shape of a long molecular axis, and Z$^3$ represents a bridging group preferably selected from —CH(OH)—, —CH(CH$_3$)—, —C(CH$_3$)$_2$—, —CO—, —CH$_2$(CO)—, —SO—, —CH$_2$(SO)—, —SO$_2$—, —CH$_2$(SO$_2$)—, —COO—, —OCO—, —COCF$_2$—, —CF$_2$CO—, —S—CO—, —CO—S—, —SOO—, —OSO—, —SOS—, —O—CO—O—, —CH$_2$—CH$_2$—, —OCH$_2$—, —CH$_2$O—, —CH=CH—, —C≡C—, —CH=CH—COO—, —OCO—CH=CH—, —CH=N—, —C(CH$_3$)=N—, —N=N— or a single bond; and Z$^4$ has one of the meanings of Z$^3$ or represents an optionally substituted straight-chain or branched alkylene group having from 1 to 20 carbon atoms, in which one or more, preferably non-adjacent, —CH$_2$— groups may be replaced by a heteroatom and/or by a group Z$^3$ as defined above and/or it is optionally possible that one or more carbon-carbon single bonds are replaced by a carbon-carbon double or a carbon-carbon triple bond; and $a^3$, $a^4$ are independently integers from 0 to 3, such that $a^3 + a^4 \leq 4$.

F is linked to group S$^2$ in formula (Ia) or to group B in formula (Ib) via group Sp$^1$ and/or group C$^3$ and/or group Z$^4$ and/or group C$^4$ and/or group Sp$^2$; and with the proviso that at least one of k$^1$, k$^2$, a$^3$ and a$^4$ is not equal to zero.

X, Y each independently represent hydrogen, fluorine, chlorine, cyano, alkyl, optionally substituted by fluorine, having from 1 to 12 carbon atoms, in which optionally one or more non-adjacent —CH$_2$— groups are replaced by a group Z$^1$, and n is 1, 2, 3 or 4.

The term "lower alkyl", as used in the context of the present invention, taken on its own or in a combination such us "lower alkoxy", etc., preferably denotes straight-chain and branched saturated hydrocarbon groups having from 1 to 6, preferably from 1 to 3, carbon atoms. Methyl, ethyl, propyl and isopropyl groups are especially preferred. In case of "lower alkoxy", methoxy, ethoxy, propoxy and isopropoxy groups are especially preferred.

The term "alicylic", as used in the context of the present invention, preferably denotes optionally substituted non-aromatic carbocyclic or heterocyclic ring systems, with 3 to 30 carbon atoms, e.g. cyclopropane, cyclobutane, cyclopentane, cyclopentene, cyclohexane, cyclohexene, cyclohexadiene, decaline, tetrahydrofuran, dioxane, pyrrolidine, piperidine or a steroidal skeleton such as cholesterol.

The term "aromatic", as used in the context of the present invention, preferably denotes optionally substituted carbocyclic and heterocyclic aromatic groups, incorporating five, six, ten or 14 ring atoms, e.g. furan, benzene, pyridine, pyrimidine, naphthalene, phenanthrene, biphenylene or tetraline units.

The term "phenylene", as used in the context of the present invention, preferably denotes a 1,2-, 1,3- or 1,4-phenylene group, which is optionally substituted. It is preferred that the phenylene group is either a 1,3- or a 1,4-phenylene group. 1,4-phenylene groups are especially preferred.

The term "halogen" denotes a chloro, fluoro, bromo or iodo substituent, preferably a chloro or fluoro substituent.

The term "polar group", as used in the context of the present invention primarily denotes a group like a nitro, cyano, or a carboxy group.

The term "hetero atom", as used in the context of the present invention primarily denotes oxygen, sulphur and nitrogen, preferably oxygen and nitrogen, in the latter case preferably in the form of —NH—.

The term "optionally substituted" as used in the context of the present invention primarily means substituted by lower alkyl, lower alkoxy, hydroxy, halogen or by a polar group as defined above.

The term "diamine" or "diamine compound" is to be understood as designating a chemical structure which has at least two amino groups, i.e. which may also have 3 or more amino groups. The at least two amino groups are preferably able to react with e.g. anhydrides as outlined in more detail below.

With respect to straight chain or branched alkyl, alkylene, alkoxy, alkoxycarbonyl, alkylcarbonyl, alkylcarbonyloxy groups it is repeatedly pointed out that some or several of the —CH$_2$— groups may be replaced e.g. by heteroatoms, but also by other groups. In such cases it is generally preferred that such replacement groups are not directly linked to each other. It is alternatively preferred that heteroatoms, and in particular oxygen atoms are not directly linked to each other.

With respect to the possibility of having several side-chains (i.e. n>1) connected to residue F, it has to be mentioned that the side chains [i.e. structures (Ia) and (Ib) without the group F] can either be linked to the group F at one atomic position within group F, e.g. two or three side chains connected to one single carbon atom within group F, or they can be linked to group F at different atomic positions within group F, e.g. at adjacent atomic positions within group F but also spaced further apart.

Another preferred embodiment of the present invention relates to diamine compounds represented by one of the general formulae (Ia) or (Ib), referring to any of the preceding definitions, and to alignment materials comprising these diamine compounds, wherein:

A, B each independently represents phenanthrylene, biphenylene, naphthylene, or phenylene, which is unsubstituted or mono- or poly-substituted by a halogen atom, hydroxy group and/or by a polar group like nitro, cyano, carboxy, and/or by acryloyloxy, methacryloyloxy, vinyl, vinyloxy, allyl, allyloxy, and/or by a cyclic, straight-chain or branched alkyl residue, which is unsubstituted, mono- or poly-substituted by fluorine and/or chlorine, having from 1 to 20 carbon atoms, wherein one or more, preferably non-adjacent —$CH_2$— groups may independently be replaced by a group, preferably selected from —O—, —CO—, —CO—O—, —O—CO—.

D represents a hydrogen atom, a halogen atom, a cyano group, —$CF_3$, —$Si(CH_3)_3$, —$Si(CH_3)_2$—O—$Si(CH_3)_3$, or a straight-chain or branched alkyl residue having from 1 to 30 carbon atoms, which is unsubstituted, mono-substituted by fluorine or chlorine, or acryloxy, methacryloxy or poly-substituted by fluorine, chlorine, and in which one or more preferably non-adjacent —$CH_2$— groups may independently be replaced by a group selected from —O—, —CO—, —CO—O—, —O—CO—, —$NR^1$—CO—, —CO—$NR^1$—, —$NR^1$—CO—O—, —O—CO—$NR^1$—, —CH═CH—, —C≡C—, and —$Si(CH_3)_2$—O—Si$(CH_3)_2$—, wherein $R^1$ represents a hydrogen atom or lower alkyl; and E represents an oxygen atom or a —N(H)— group.

$S^1$, $S^2$ each independently represents a single bond or a spacer unit such as a straight-chain or branched alkylene group, having from 1 to 24 carbon atoms, wherein one or more —$CH_2$— groups may independently be replaced by a group represented by the formula (II), wherein:

$C^1$, $C^2$ are selected from:

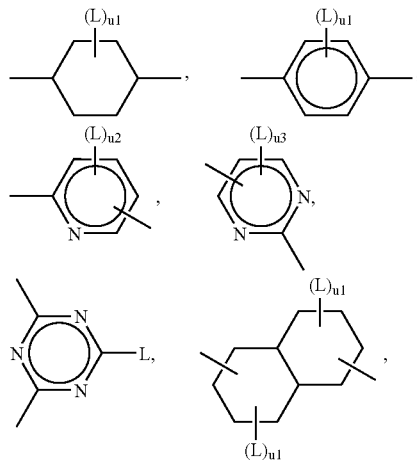

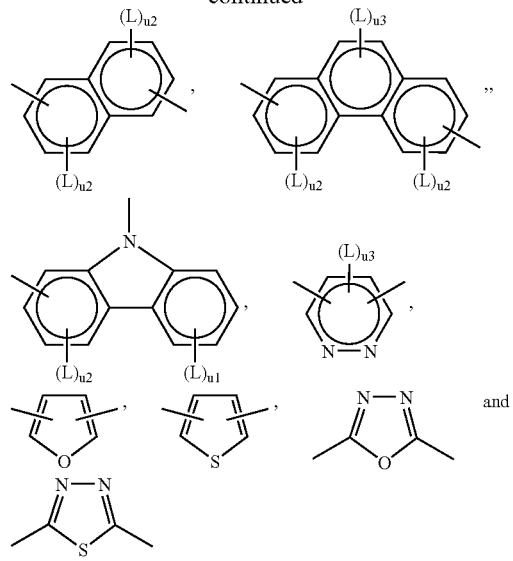

wherein:
"—" denotes the connecting bonds of $C^1$ and $C^2$ to the adjacent groups; and L is —$CH_3$, —$COCH_3$, nitro, cyano, halogen, $CH_2$═CH—, $CH_2$═C($CH_3$)—, $CH_2$═CH—(CO)O—, $CH_2$═CH—O—, $CH_2$═C($CH_3$)—(CO)O—, or $CH_2$═C($CH_3$)—O—, u1 is an integer from 0 to 4; and
u2 is an integer from 0 to 3; and
u3 is an integer from 0 to 2; and $Z^1$, $Z^2$ each independently represents —O—, —CO—, —COO—, —OCO—, —$COCF_2$—, —$CF_2CO$—, —$CH_2$—$CH_2$—, —$OCH_2$—, —$CH_2O$—, —CH═CH—, —C≡C—, —CH═CH—COO—, —OCO—CH═CH— or a single bond;

with the proviso that heteroatoms are not directly linked to each other, and $a^1$, $a^2$ each independently represents an integer from 0 to 3, such that $a^1 + a^2 \leq 4$.

F represents an optionally substituted aliphatic, aromatic or alicyclic diamino group having from 1 to 40 carbon atoms, preferably selected from formula (III), wherein:
$k^1$, $k^2$ are 0 or 1, and
$t^1$, $t^2$ are 0, and
$R^5$, $R^6$ are identical and represent a hydrogen atom, a methyl, an ethyl or an isopropyl group; and
$C^3$, $C^4$ independently from each other are selected from:

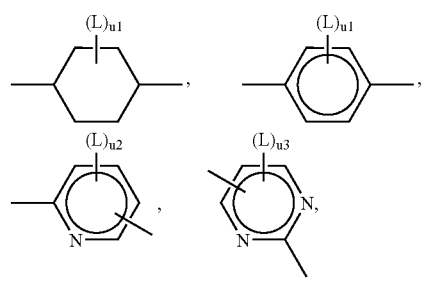

-continued

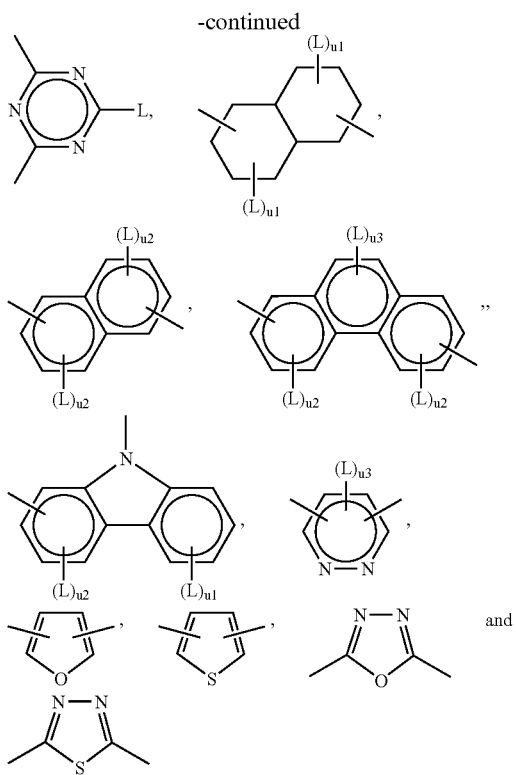

wherein:
"—" denotes the connecting bonds of $C^3$ and $C^4$ to the adjacent groups; and L is —$CH_3$, —$COCH_3$, nitro, cyano, halogen, $CH_2$=CH—, $CH_2$=C($CH_3$)—, $CH_2$=CH—(CO)O—, $CH_2$=CH—O—, $CH_2$=C($CH_3$)—(CO)O— or $CH_2$=C($CH_3$O)—, u1 is an integer from 0 to 4; and
u2 is an integer from 0 to 3; and
u3 is an integer from 0 to 2; and $Z^3$ represents a group selected from —CH(OH)—, —CH($CH_3$)—, —C($CH_3$)$_2$—, —CO—, —COO—, —$COCF_2$—, —$CF_2CO$— or a single bond; and $Z^4$ has one of the meanings of $Z^3$ or represents an optionally substituted straight chain or branched alkylene group having from 1 to 16 carbon atoms, in which one or more, preferably non-adjacent, —$CH_2$— groups may be replaced by an oxygen atom and/or it is optionally possible that one or more carbon-carbon single bonds are replaced by a carbon-carbon double or a carbon-carbon triple bond; and $a^3$, $a^4$ each independently represents an integer from 0 to 2, such that $a^3+a^4 \leq 3$.

F is linked to $S_2$ in formula (Ia) or to B in formula (Ib) via group $Sp^1$ and/or group $C^3$ and/or group $Z^4$ and/or group $C^4$ and/or group $Sp^2$; and with the proviso that at least one of $k^1$, $k^2$, $a^3$ and $a^4$ is not equal to zero.

X, Y are hydrogen atoms, and
n is 1, 2 or 3.

Another preferred embodiment of the present invention relates to diamine compounds represented by one of the general formulae (Ia) or (Ib), referring to any of the preceding definitions, and to alignment materials comprising these diamine compounds, wherein:

A, B each independently represents a biphenylene, naphthylene or phenylene group, which is unsubstituted or mono- or poly-substituted by a halogen atom, a hydroxy group, and/or by acryloyloxy, and/or methacryloyloxy groups, and/or by straight-chain or branched alkyl, alkoxy, alkylcarbonyloxy, and/or alkyloxycarbonyl groups having from 1 to 20 carbon atoms.

D represents a hydrogen atom, a halogen atom, —$CF_3$, —Si($CH_3$)$_3$, —Si($CH_3$)$_2$—O—Si($CH_3$)$_3$, or a straight-chain or branched alkyl residue having from 1 to 20 carbon atoms, preferably selected from formula (IV):

$$P^1\text{-}Sp^3\text{-}X^3\text{—} \quad (IV)$$

wherein:
$P^1$ represents hydrogen, halogen, a silane group or a polymerizable group, such as: $CH_2$=CH—, $CH_2$=C($CH_3$)—, $CH_2$=CH—(CO)O—, $CH_2$=CH—O—, $CH_2$=C($CH_3$)—(CO)O— or $CH_2$=C($CH_3$)—O—;

$Sp^3$ represents a straight chain or branched alkyl group having from 1 to 30 carbon atoms which is mono- or poly-substituted by fluorine and/or chlorine and wherein optionally one or more, preferably non-adjacent —$CH_2$— groups present in the hydrocarbon chain may independently be replaced by one or more groups selected from —O—, —CO—, —CO—O—, —O—CO—, —$NR^1$—CO—, —CO—$NR^1$—, —$NR^1$—CO—O—, —O—CO—$NR^1$—, —CH=CH—, —C≡C— and —Si($CH_3$)$_2$—O—Si($CH_3$)$_2$—, wherein:

$R^1$ represents a hydrogen atom or lower alkyl; with the proviso that oxygen atoms are not directly linked to each other; and wherein:

especially preferred $Sp^3$ groups are $C_1$-$C_{20}$-alkyl, $C_1$-$C_{20}$-alkoxy, $C_1$-$C_{20}$-alkoxycarbonyl, $C_1$-$C_{20}$-alkylcarbonyl or $C_1$-$C_{20}$-alkylcarbonyloxy groups, for example methyl, ethyl, propyl, butyl, pentyl, hexyl, heptyl, octyl, nonyl, decyl, undecyl, dodecyl, methoxy, ethoxy, n-propoxy, isopropoxy, butoxy, pentyloxy, hexyloxy, heptyloxy, octyloxy, nonyloxy, decyloxy, undecyloxy, dodecyloxy, methoxycarbonyl, ethoxycarbonyl, propoxycarbonyl, butoxycarbonyl, pentyloxycarbonyl, hexyloxycarbonyl, octyloxycarbonyl, nonyloxycarbonyl, decyloxycarbonyl, undecyloxy carbonyl, dodecyloxycarbonyl, acetyl, propionyl, butyryl, valeryl, hexanoyl, heptanoyl, octanoyl, nonanoyl, decanoyl, undecanoyl, dodecanoyl, terdecanoyl, acetoxy, propionyloxy, butyryloxy, valeryloxy, hexanoyloxy, heptanoyloxy, octanoyloxy, nonanoyloxy, decanoyloxy, undecanoyloxy, dodecanoyloxy, terdecanoyloxy and the like, which may be mono- or poly-substituted by fluorine; and $X^3$ has one of the meanings of $X^1$.

E represents an oxygen atom or a —N(H)— group.

$S^1$, $S^2$ each independently represents a single bond or a spacer unit such a straight-chain or branched alkylene groups, having from 1 to 14 carbon atoms, wherein one or more —$CH_2$— groups may independently be replaced by a group represented by formula (II), wherein:

$C^1$, $C^2$ each independently represents a 1,4-phenylene, 1,4-cyclohexylene or a 4,4'-biphenylene group; and $Z^1$, $Z^2$ each independently represents —COO—, —OCO—, —$CH_2$—$CH_2$—, —$OCH_2$—, —$CH_2O$—, —CH=CH—, —C≡C—, —CH=CH—COO—, —OCO—CH=CH— or a single bond; and $a^1$, $a^2$ are independently 0 or 1.

F represents an optionally substituted aliphatic, aromatic or alicyclic diamino group having from 1 to 40 carbon atoms, represented by formula (III) and preferably made from or selected from the following group of structures: aniline, p-phenylenediamine, m-phenylenediamine, benzidine, diaminofluorene, or their derivatives, with the proviso that compounds listed which do not carry two amino groups are taken as derivatives with at least one additional amino group, and more preferably made from or selected from the following commercially available amino compounds:

4-amino-2,3,5,6-tetrafluorobenzoic acid, 4-amino-3,5-diiodobenzoic acid, 3,4-diaminobenzoic acid, 4-amino-3-methylbenzoic acid, 4-amino-2-chlorobenzoic acid, 4-aminosalicylic acid, 4-aminobenzoic acid, 4-aminophthalic acid, 1-(4-aminophenyl)ethanol, 4-aminobenzyl alcohol, 4-amino-3-methoxybenzoic acid, 4-aminophenyl ethyl carbinol, 4-amino-3-nitrobenzoic acid, 4-amino-3,5-dinitrobenzoic acid, 4-amino-3,5-dichlorobenzoic acid, 4-amino-3-hydroxybenzoic acid, 4-aminobenzyl alcohol hydrochloride, 4-aminobenzoic acid hydrochloride, pararosaniline base, 4-amino-5-chloro-2-methoxybenzoic acid, 4-(hexafluoro-2-hydroxyisopropyl)aniline, piperazine-p-amino benzoate, 4-amino-3,5-dibromobenzoic acid, isonicotinic acid hydrazide p-aminosalicylate salt, 4-amino-3,5-diiodosalicylic acid, 4-amino-2-methoxybenzoic acid, 2-[2-(4-aminophenyl)-2-hydroxy-1-(hydroxymethyl)ethyl]isoindoline-1,3-dione, 4-amino-2-nitrobenzoic acid, 2,4-diaminobenzoic acid, p-aminobenzoic acid, [3,5-3h]-4-amino-2-methoxybenzoic acid, L-(+)-threo-2-amino-1-(4-aminophenyl)-1,3-propanediol, L-(+)-threo-2-(N,N-dimethylamino)-1-(4-aminophenyl)-1,3-propanediol, ethyl 2-(4-aminophenyl)-3,3,3-trifluoro-2-hydroxypropanoate, ethyl 2-(4-amino-3-methylphenyl)-3,3,3-trifluoro-2-hydroxypropanoate, ethyl 2-(4-amino-3-methoxyphenyl)-3,3,3-trifluoro-2-hydroxypropanoate, 3,4-diaminobenzyl alcohol dihydrochloride, 4-aminonaphthalene-1,8-dicarboxylic acid, 4-amino-3-chloro-5-methylbenzoic acid, 4-amino-2,6-dimethylbenzoic acid, 4-amino-3-fluorobenzoic acid, 4-amino-5-bromo-2-methoxybenzenecarboxylic acid, 2,7-diaminofluorene, 4,4'-diaminooctafluorobiphenyl, 3,3'-diaminobenzidine, 3,3',5,5'-tetramethylbenzidine, 3,3'-dimethoxybenzidine, o-tolidine, 3,3'-dinitrobenzidine, 2-nitrobenzidine, 3,3'-dihydroxybenzidine, o-tolidine sulfone, benzidine, 3,3'-dichlorobenzidine, 2,2',5,5'-tetrachlorobenzidine, benzidine-3,3'-dicarboxylic acid, 4,4'-diamino-1,1'-binaphthyl, 4,4'-diaminodiphenyl-3,3'-diglycolic acid, dihydroethidium, o-dianisidine, 2,2'-dichloro-5,5'-dimethoxybenzidine, 3-methoxybenzidine, 3,3'-dichlorobenzidine (diphenyl-d6), 2,7-diamino-9-fluorenone, 3,5,3',5'-tetrabromo-biphenyl-4,4'-diamine, 2,2'-bis(trifluoromethyl)benzidine, 2,2'-dichloro[1,1'-biphenyl]-4,4'-diamine, 3,9-diamino-1,11-dimethyl-5,7-dihydrodibenzo(a,c)cyclohepten-6-one, 3,3'-bis(trifluoromethyl)benzidine, dibenzo(1,2)dithiine-3,8-diamine, 3,3'-tolidine-5-sulfonic acid, 3,3'-dichlorobenzidine-d6, tetramethylbenzidine, 3,3'-diaminobenzophenone, 3,3'-diaminodiphenylmethane, 4,4-bis-(3-amino-4-hydroxyphenyl)-valeric acid, 2,2-bis(3-amino-4-hydroxyphenyl)hexafluoropropane, 2,2-bis(3-amino-4-methylphenyl)hexafluoropropane, tetrabromo methylenedianiline, 2,7-diamino-9-fluorenone, 2,2-bis(3-aminophenyl)hexafluoropropane, bis-(3-amino-4-chloro-phenyl)-methanone, bis-(3-amino-4-dimethylamino-phenyl)-methanone, 3-[3-amino-5-(trifluoromethyl)benzyl]-5-(trifluoromethyl)aniline, 1,5-diaminonaphthalene or their derivatives, again with the proviso that compounds listed which do not carry two amino groups are taken as derivatives with at least one additional amino group, and n 1 or 2.

Most preferred diamine compounds in the context of the present invention are represented by one of the general formulae (Ia) or (Ib), referring to any of the preceding definitions, and to alignment materials comprising these diamine compounds, wherein:

A, B each independently represents 1,4-phenylene, which is unsubstituted or mono- or poly-substituted by a halogen atom, and/or by acryloyloxy or methacryloyloxy, and/or by an alkoxy, alkylcarbonyloxy or an alkyloxycarbonyl group, having from 1 to 10 carbon atoms.

D represents fluorine, —Si(CH$_3$)$_3$, —Si(CH$_3$)$_2$—O—Si(CH$_3$)$_3$, or a straight-chain or branched alkyl residue having from 1 to 16 carbon atoms, preferably selected from formula (IV), wherein:

P$^1$ represents hydrogen or fluorine; and

Sp$^3$ represents a $C_1$-$C_{12}$-alkyl, $C_1$-$C_{12}$-alkoxy, $C_1$-$C_{12}$-alkoxycarbonyl, $C_1$-$C_{12}$-alkylcarbonyl or $C_1$-$C_{12}$-alkylcarbonyloxy group, which may be mono- or poly-substituted by fluorine.

E represents an oxygen atom.

S$^1$, S$^2$ each independently represents a single bond or a spacer unit such a straight-chain alkylene group, having from 1 to 12 carbon atoms, wherein one or more —CH$_2$— groups may independently be replaced by a group of formula (II), wherein:

C$^1$, C$^2$ each independently represents 1,4-phenylene; and

Z$^1$, Z$^2$ each independently represents—COO—, —OCO—, —CH$_2$—CH$_2$—, —OCH$_2$—, —CH$_2$O—, —CH=CH—, —C≡C—, —CH=CH—COO—, —OCO—CH=CH—, or a single bond; and a$^1$, a$^2$ each independently represents 0 or 1, and n is 1.

Another preferred embodiment of the present invention relates to diamine compounds represented by the general formulae (Ia) and (Ib), which may be used in the subsequent manufacturing processes as such or in combination with one or more additional other diamines.

Preferred examples of additional other diamines are:

ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10-decylenediamine, 1,11-undecylenediamine, 1,12-dodecylenediamine, α,α'-diamino-m-xylene, α,α'-diamino-p-xylene, (5-amino-2,2,4-trimethylcyclopentyl)methylamine, 1,2-diaminocyclohexane, 4,4'-diaminodicyclohexylmethane, 1,3-bis(methylamino)cyclohexane, 4,9-dioxadodecane-1,12-diamine, 3,5-diaminobenzoic acid methyl ester, 3,5-diaminobenzoic acid hexyl ester, 3,5-diaminobenzoic acid dodecyl ester, 3,5-diaminobenzoic acid isopropyl ester, 4,4'-methylenedianiline, 4,4'-ethylenedianiline, 4,4'-diamino-3,3'-dimethyldiphenylmethane, 3,3',5,5'-tetramethylbenzidine, 4,4'-diaminodiphenyl sulfone, 4,4'-diaminodiphenyl ether, 1,5-diaminonaphthalene, 3,3'-dimethyl-4,4'-diaminobiphenyl, 3,4'-diaminodiphenyl ether, 3,3'-diaminobenzophenone, 4,4'-diaminobenzophenone, 4,4'-diamino-2,2'-dimethylbibenzyl, bis[4-(4-aminophenoxy)phenyl]sulfone, 1,4-bis(4-aminophenoxy)benzene, 1,3-bis(4-aminophenoxy)benzene, 1,3-bis(3-aminophenoxy)benzene, 2,7-diaminofluorene, 9,9-bis(4-aminophenyl)fluorene, 4,4'-methylene-bis(2-chloroaniline), 4,4'-bis(4-aminophenoxy)biphenyl, 2,2',5,5'-tetrachloro-4,4'- diaminobiphenyl, 2,2'-dichloro-4,4'-diamino-5,5'-dimethoxybiphenyl, 3,3'-dimethoxy-4,4'-diaminobiphenyl, 4,4'-(1,4-phenyleneisopropylidene)bisaniline, 4,4'-(1,3-phenyleneisopropylidene)bisaniline, 2,2-bis[4-(4-aminophenoxy)phenyl]pro pane, 2,2-bis[3-(4-aminophenoxy)phenyl]hexafluoropropane, 2,2-bis[3-amino-4-methylphenyl]hexafluoropropane, 2,2-bis(4-aminophenyl)hexafluoropropane, 2,2'-bis[4-(4-amino-2-trifluoromethylphenoxy)phenyl]hexafluoropropane, 4,4'-diamino-2,2'-bis(trifluoromethyl)biphenyl, and 4,4'-bis[(4-amino-2-trifluoromethyl)phenoxy]-2,3,5,6,2',3',5',6'-octafluorobiphenyl, as well as diamines disclosed in U.S. Pat. No. 6,340,506, WO 00/59966 and WO 01/53384, all of which are explicitly incorporated herein by reference.

A further preferred embodiment of the present invention relates to a polymer material or oligomer material from the class of polyamic acids, polyamic acid esters or polyimides, (and any mixtures thereof) obtained by or obtainable by the reaction of at least one diamine compound represented by the general formulae (Ia) and (Ib) and optionally of one or more additional other diamines (as e.g. given above), with one or more tetracarboxylic acid anhydrides of the general formula (V)

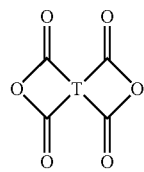

(V)

wherein:
T represents a tetravalent organic radical.

The tetravalent organic radical T is preferably derived from an aliphatic, alicyclic or aromatic tetracarboxylic acid dianhydride.

Preferred examples of aliphatic or alicyclic tetracarboxylic acid dianhydrides are:
1,1,4,4-butanetetracarboxylic acid dianhydride, ethylenemaleic acid dianhydride, 1,2,3,4-cyclobutanetetracarboxylic acid dianhydride, 1,2,3,4-cyclopentanetetracarboxylic acid dianhydride, 2,3,5-tricarboxycyclopentylacetic acid dianhydride, 3,5,6-tricarboxynorbornylacetic acid dianhydride, 2,3,4,5-tetrahydrofurantetracarboxylic acid dianhydride, rel-[1S,5R,6R]-3-oxabicyclo[3.2.1]octane-2,4-dione-6-spiro-3'-(tetrahydrofuran2',5'-dione), 4-(2,5-dioxotetrahydrofuran-3-yl)tetrahydronaphthalene-1,2-dicarboxylicacid dianhydride, 5-(2,5-dioxotetrahydrofuran-3-yl)-3-methyl-3-cyclohexene-1,2-dicarboxylic-acid dianhydride, bicyclo[2.2.2]oct-7-ene-2,3,5,6-tetracarboxylic acid dianhydride, bicyclo[2.2.2]octane-2,3,5,6-tetracarboxylic acid dianhydride, 1,8-dimethylbicyclo[2.2.2]oct-7-ene-2,3,5,6-tetracarboxylic acid dianhydride, and the like.

Preferred examples of aromatic tetracarboxylic acid dianhydrides are:
pyromellitic acid dianhydride, 3,3',4,4'-benzophenonetetracarboxylic acid dianhydride, 4,4'-oxydiphthalic acid dianhydride, 3,3',4,4'-diphenylsulfonetetracarboxylic acid dianhydride, 1,4,5,8-naphthalenetetracarboxylic acid dianhydride, 2,3,6,7-naphthalenetetracarboxylic acid dianhydride, 3,3',4,4'-dimethyldiphenylsilanetetracarboxylic acid dianhydride, 3,3',4,4'-tetraphenylsilanetetracarboxylic acid dianhydride, 1,2,3,4-furantetracarboxylic acid dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-biphenyltetracarboxylic acid dianhydride, ethylene glycol bis(trimellitic acid) dianhydride, 4,4'-(1,4-phenylene)bis(phthalic acid) dianhydride, 4,4'-(1,3-phenylene)bis(phthalic acid) dianhydride, 4,4'-(hexafluoroisopropylidene)diphthalic acid dianhydride, 4,4'-oxydi(1,4-phenylene)bis(phthalic acid) dianhydride, 4,4'-methylenedi(1,4-phenylene)bis(phthalic acid) dianhydride, and the like.

More preferably the tetracarboxylic acid dianhydrides used to form the tetravalent organic radical T are selected from:
1,2,3,4-cyclobutanetetracarboxylic acid dianhydride, 1,2,3,4-cyclopentanetetracarboxylic acid dianhydride, 2,3,5-tricarboxycyclopentylacetic acid dianhydride, 5-(2,5-dioxotetrahydrofuran-3-yl)-3-methyl-3-cyclohexene-1,2-dicarboxylic acid dianhydride, 4-(2,5-dioxotetrahydrofuran-3-yl)tetrahydronaphthalene-1,2-dicarboxylic acid dianhydride, 4,4'-(hexafluoroisopropylidene)diphthalic acid dianhydride and bicyclo[2.2.2]oct-7-ene-2,3,5,6-tetracarboxylic acid dianhydride.

Preferred polyamic acids, polyamic acid esters or polyimides (and any mixtures thereof) of the present invention relate to those which comprise as side-chains a photo-reactive group that can be photo-isomerized and/or photo-dimerized on exposure to visible light, UV light or laser light. It is preferred that at least 30% of the repeating units include a side chain with a photo-reactive group.

Preferably, the photo-reactive groups are able to undergo photo-cyclization, in particular [2+2]-photo-cyclisation.

Preferably, the photo-reactive groups are sensitive to visible and/or UV light, in particular to linearly polarized UV light.

The side-chain polymers or oligomers according the invention can be present in the form of homopolymers as well as in the form of copolymers. The term "copolymers" is to be understood as meaning especially statistical copolymers.

The diamine compounds according to the present invention may be prepared using methods that are known to a person skilled in the art.

The polyamic acids, polyamic acid esters and polyimides according to the present invention may be prepared in line with known methods, such as those described in *Plast. Eng.* 36 (1996), (Polyimides, fundamentals and applications), Marcel Dekker, Inc.

For example, the poly-condensation reaction for the preparation of the polyamic acids is carried out in solution in a polar aprotic organic solvent, such as γ-butyrolactone, N,N-dimethylacetamide, N-methylpyrrolidone or N,N-dimethylformamide. In most cases equimolar amounts of the dianhydride and the diamine are used, i.e. one amino group per anhydride group. If it is desired to stabilize the molecular weight of the polymer or oligomer, it is possible for that purpose to either add an excess or a less-than-stoichiometric amount of one of the two components or to add a mono-functional compound in the form of a dicarboxylic acid monoanhydride or in the form of a mono-amine. Examples of such mono-functional compounds are maleic acid anhydride, phthalic acid anhydride, aniline and the like. Preferably the reaction is carried out at temperatures of less than 100° C.

The cyclisation of the polyamic acids to form the polyimides can be carried out by heating, i.e. by condensation with removal of water or by other imidisation reactions using appropriate reagents. When carried out purely thermally, the imidisation of the polyamic acids may not always be complete, i.e. the resulting polyimides may still contain proportions of polyamic acid. In general the imidisation reactions are carried out at temperatures between 60 and 250° C., preferably at temperatures of less than 200° C. In order to achieve imidisation at lower temperatures additional reagents that facilitate the removal of water are added to the reaction mixture. Such reagents are, for example, mixtures consisting of acid anhydrides, such as acetic acid anhydride, propionic acid anhydride, phthalic acid anhydride, trifluoroacetic acid anhydride or tertiary amines, such as triethylamine, trimethylamine, tributylamine, pyridine, N,N-dimethylaniline, lutidine, collidine etc. The amount of aforementioned additional reagents that facilitate the removal of water is preferably at least four equivalents of acid anhydride and two equivalents of amine per equivalent of polyamic acid to be condensed.

The imidisation reaction can be carried out prior or after the application to a support.

The polyamic acids and the polyimides of the present invention have an intrinsic viscosity preferably in the range of 0.05 to 10 dL/g, more preferably in the range of 0.05 to 5 dL/g. Herein, the intrinsic viscosity ($\eta_{inh}$=ln $\eta_{rel}$/C) is determined by measuring a solution containing a polymer or an oligomer in a concentration of 0.5 g/100 ml solution for the evaluation of its viscosity at 30° C. using N-methyl-2-pyrrolidone as solvent.

The polyamic acid chains or polyimide chains of the present invention preferably contain from 2 to 2000 repeating units, especially from 3 to 200 repeating units.

Additives such as silane-containing compounds and epoxy-containing cross-linking agents may be added to the polymers or the oligomers of the invention in order to improve the adhesion of the polymer or the oligomer to the substrates.

Suitable silane-containing compounds are described in *Plast. Eng.* 36 (1996), (Polyimides, fundamentals and applications), Marcel Dekker, Inc.

Suitable epoxy-containing cross-linking agents include 4,4'-methylene-bis-(N,N-diglycidylaniline), trimethylolpropane triglycidyl ether, benzene-1,2,4,5-tetracarboxylic acid 1,2,4,5-N,N'-diglycidyidiimide, polyethylene glycol diglycidyl ether, N,N-diglycidylcyclohexylamine and the like.

Additional additives such one or more photo-sensitizers and/or one or more photo-radical generators and/or one or more cationic photo-initiators may also be added to the polymers or oligomers of the invention.

Suitable photo-active additives include 2,2-dimethoxyphenylethanone, a mixture of diphenylmethanone and N,N-dimethylbenzenamine or ethyl 4-(dimethylamino)benzoate, xanthone, thioxanthone, Irgacure® 184, 369, 500, 651 and 907 (Ciba), Michler's ketone, triaryl sulfonium salt and the like.

The polymers or oligomers according to the invention may be used in form of polymer layers or oligomer layers alone or in combination with other polymers, oligomers, monomers, photo-active polymers, photo-active oligomers and/or photo-active monomers, depending upon the application to which the polymer or oligomer layer is to be added. Therefore it is understood that by varying the composition of the polymer or oligomer layer it is possible to control specific and desired properties, such as an induced pre-tilt angle, good surface wetting, a high voltage holding ratio, a specific anchoring energy, etc.

Polymer or oligomer layers may readily be prepared from the polymers or oligomers of the present invention and a further embodiment of the invention relates to a polymer or oligomer layer comprising a polymer or oligomer according to the present invention in a cross-linked form.

The polymer or oligomer layer is preferably prepared by applying one or more polymers or oligomers according to the invention to a support and, after any imidisation step which may be necessary, cross-linking the polymer or oligomer or polymer mixture or oligomer mixture by irradiation with linearly polarized light. It is possible to vary the direction of orientation and the tilt angle within the polymer or oligomer layer by controlling the direction of the irradiation of the linearly polarized light. It is understood that by selectively irradiating specific regions of the polymer or oligomer layer it is possible to align very specific regions of the layer and to provide layers with a defined tilt angle. The induced orientation and tilt angle are retained in the polymer or oligomer layer by the process of cross-linking.

It is understood that the polymer or oligomer layers of the present invention (in form of a polymer gel, a polymer network, a polymer film, etc.) can also be used as orientation layers for liquid crystals and a further preferred embodiment of the invention relates to an orientation layer comprising one or more polymers or oligomers according to the invention in a cross-linked form.

Such orientation layers can be used in the manufacture of unstructured or structured optical- or electro-optical elements, preferably in the production of hybrid layer elements.

The orientation layers are suitably prepared from a solution of the polymer or oligomer material. The polymer or oligomer solution is applied to a support optionally coated with an electrode [for example a glass plate coated with indium-tin oxide (ITO)] so that homogeneous layers of 0.05 to 50 μm thickness are produced. In this process different coating techniques like spin-coating, meniscus-coating, wire-coating, slot-coating, offset-printing, flexo-printing, gravur-printing may be used. Then, or optionally after a prior imidisation step, the regions to be oriented are irradiated, for example, with a high-pressure mercury vapour lamp, a xenon lamp or a pulsed UV laser, using a polarizer and optionally a mask for creating images of structures.

The irradiation time is dependent upon the output of the individual lamps and can vary from a few seconds to several hours. The photo-reaction (dimerisation, polymerization, cross-linking) can also be carried out, however, by irradiation of the homogeneous layer using filters that, for example, allow only the radiation suitable for the cross-linking reaction to pass through.

It is understood that the polymer or oligomer layers of the invention may be used in the production of optical or electro-optical devices having at least one orientation layer as well as unstructured and structured optical elements and multi-layer systems.

A further embodiment of the invention relates to an optical or electro-optical device comprising one or more polymers or oligomers according to the present invention in cross-linked form. The electro-optical devices may comprise more than one layer. The layer, or each of the layers may contain one or more regions of different spatial orientation.

The diamine compounds and polymers or oligomers in accordance with the present invention are illustrated further by the following detailed Examples, which shall not be construed to limit the scope of the invention as outlined in the claims.

DETAILED DESCRIPTION OF THE PREFERRED EMBODIMENTS

The chemical structure of the compounds related to the present invention and listed below has been verified using IR-, $^1$H NMR- and/or Mass-Spectroscopy.

EXAMPLE 1

Synthesis

Preparation of 6-{4-[(1E)-3-(4-pentyloxyphenoxy)-3-oxoprop-1-enyl]phenoxy}hexyl 3,5 diaminobenzoate in accordance with the following procedure

1.1 (2E)-3-{4-[(ethoxycarbonyl)oxy]phenyl}acrylic acid

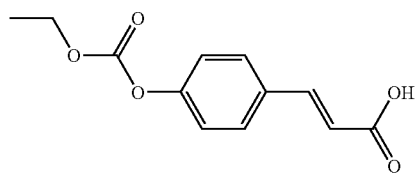

67 g (0.41 mol) p-cumaric acid were added to a mixture of 50.4 g (0.90 mol) potassium hydroxide and 600 ml water. 53.1 g (0.50 mol) ethyl chloroformate were added dropwise at 0° C. The reaction temperature rose to 10° C. The reaction mixture was subsequently allowed to react for 2 h at 25° C. and acidified to pH=1 with 200 ml hydrochloric acid 7 N. The product was filtered off, washed with water and dried under vacuum to give 95.3 g of (2E)-3-{4-[(ethoxycarbonyl)oxy]phenyl}acrylic acid as white powder.

1.2 4-pentoxyphenyl (2E)-3-{4-[(ethoxycarbonyl)oxy]phenyl}acrylate

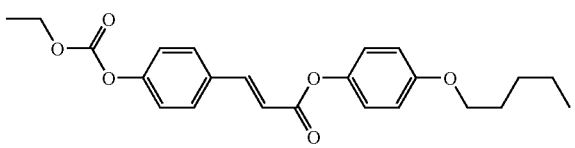

23.00 g (97 mmol) 4-pentoxyphenol, 17.6 g (97 mmol) (2E)-3-{4-[(ethoxycarbonyl)oxy]phenyl}acrylic acid and 1.18 g (9.7 mmol) 4-dimethylaminopyridine were dissolved in 300 ml of dichloromethane. A suspension of 18.6 g (97 mmol) N-(3-dimethylaminopropyl)-N'-ethylcarbo-diimide hydrochloride and 200 ml dichloromethane were added dropwise in the course of 40 minutes. After 22 h at room temperature, the reaction mixture was partitioned between dichloromethane and water; the organic phase was washed repeatedly with water, dried over sodium sulphate, filtered and concentrated by rotary evaporation. Chromatography of the residue on 200 g silica gel using cyclohexane:ethyl acetate (7:3) then (1:1) as eluent yielded 36.4 g (94%) 4-pentoxyphenyl (2E)-3-{4-[(ethoxycarbonyl)oxy]phenyl}acrylate as colourless crystals.

1.3. 4-pentoxyphenyl (2E)-3-{4-hydroxyphenyl}acrylate

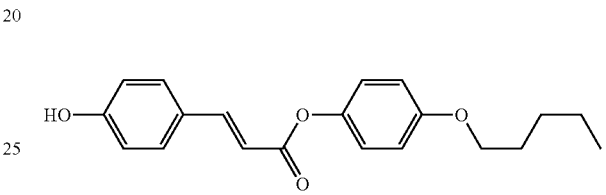

7.65 g (23.45 mmol) 4-pentoxyphenyl (2E)-3-{4-[(ethoxycarbonyl)oxy]phenyl}acrylate, 70 ml pyridine and 40 ml acetone were mixed. A solution of 12.5 ml ammonium hydroxide 25% in water and 30 ml acetone were added dropwise. The reaction mixture was subsequently allowed to react for 18 h at 25° C. and acidified to pH=1 with hydrochloric acid 7 N. The product was filtered off, washed with water and dried under vacuum to give 7.35 g 4-pentoxyphenyl (2E)-3-{4-hydroxyphenyl}acrylate as colourless powder.

1.4 4-pentoxyphenyl (2E)-3-{4-(6-chlorohexyloxy)phenyl}acrylate

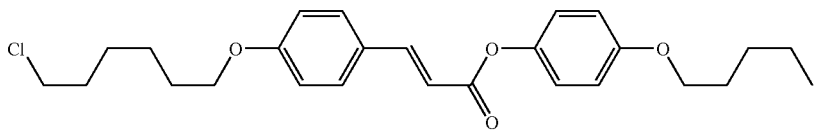

7.35 g (22.5 mmol) 4-pentoxyphenyl (2E)-3-{4-hydroxyphenyl}acrylate, 3.36 g (24.6 mmol) 6-chloro-1-hexanol and 6.45 g (24.6 mmol) of triphenylphosphine were dissolved in 100 ml of tetrahydrofurane. The colourless solution was subsequently cooled to 0° C. and 4.28 g (24.6 mmol) of a 40% solution of azodicarboxylic acid diethyl ester in toluene were added dropwise thereto over a period of 25 minutes. The mixture was subsequently allowed to react for 4 h at 0° C. The reaction mixture was reduced in volume by evaporation. The resulting residue was added to a mixture of methanol and water (3:2) and was then extracted with a mixture of tert.-butyl-methylether:hexane 1:1. The tert.-butyl-methylether:hexane phase was washed repeatedly with water, dried over magnesium sulphate, filtered and concentrated by rotary evaporation to yield 7.5 g 4-pentoxyphenyl (2E)-3-{4-(6-chlorohexyloxy)phenyl}acrylate as yellowish crystals.

1.5 6-{4-[(1E)-3-(4-pentyloxyphenoxy)-3-oxoprop-1-enyl]phenoxy}hexyl 3,5 diaminobenzoate

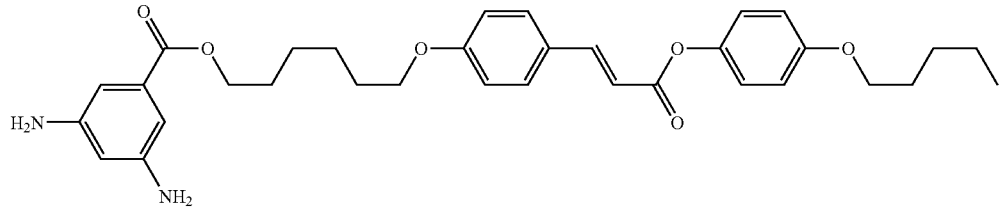

7.50 g (16.85 mmol) 4-pentoxyphenyl (2E)-3-{4-(6-chlorohexyloxy)phenyl}acrylate, 2.82 g (18.54 mmol) 3,5-diaminobenzoic acid and 0.62 g (1.69 mmol) tetrabutylammonium iodide were dissolved in 80 ml dimethylformamide. 3.00 ml (20.22 mmol) 1,8-diazabicyclo[5.4.0]undec-7-ene(1,5-5) (DBU) were added dropwise in the course of 10 minutes. The reaction temperature rose to 30° C. The mixture was then heated at 80° C. for 22 h. The reaction mixture was cooled and then partitioned between ethyl acetate and a saturated sodium bicarbonate solution; the organic phase was washed repeatedly with water, dried over sodium sulphate, filtered and concentrated by rotary evaporation. Chromatography of the residue on 1 kg silica gel using cyclohexane:ethyl acetate 1:1 as eluent yielded 6.6 g of 6-{4-[(1E)-3-(4-pentyloxyphenoxy)-3-oxoprop-1-enyl]phenoxy}hexyl 3,5 diamino-benzoate.

The Following Diamines were Synthesized in an Analogous Manner:

2-{4-[(1E)-3-(4-pentyloxyphenoxy)-3-oxoprop-1-enyl]phenoxy}ethyl 3,5 diaminobenzoate.
3-{4[(1E)-3-(4-pentyloxyphenoxy)-3-oxoprop-1-enyl]phenoxy}propyl 3,5 diaminobenzoate.
5-{4-[(1E)-3-(4-pentyloxyphenoxy)-3-oxoprop-1-enyl]phenoxy}pentyl 3,5 diaminobenzoate.
7-{4-[(1E)-3-(4-pentyloxyphenoxy)-3-oxoprop-1-enyl]phenoxy}heptyl 3,5 diaminobenzoate.
8-{4-[(1E)-3-(4-pentyloxyphenoxy)-3-oxoprop-1-enyl]phenoxy}octyl 3,5 diaminobenzoate.
11-{4-[(1E)-3-(4-pentyloxyphenoxy)-3-oxoprop-1-enyl]phenoxy}undecyl 3,5 diaminobenzoate.
2-{4-[(1E)-3-(4-butyloxyphenoxy)-3-oxoprop-1-enyl]phenoxy}ethyl 3,5 diaminobenzoate.
3-{4-[(1E)-3-(4-butyloxyphenoxy)-3-oxoprop-1-enyl]phenoxy}propyl 3,5 diaminobenzoate.
5-{4-[(1E)-3-(4-butyloxyphenoxy)-3-oxoprop-1-enyl]phenoxy}pentyl 3,5 diaminobenzoate.
7-{4-[(1E)-3-(4-butyloxyphenoxy)-3-oxoprop-1-enyl]phenoxy}heptyl 3,5 diaminobenzoate.
8-{4-[(1E)-3-(4-butyloxyphenoxy)-3-oxoprop-1-enyl]phenoxy}octyl 3,5 diaminobenzoate.
11-{4-[(1E)-3-(4-butyloxyphenoxy)-3-oxoprop-1-enyl]phenoxy}undecyl 3,5 diaminobenzoate.
2-{4-[(1E)-3-(4-hexyloxyphenoxy)-3-oxoprop-1-enyl]phenoxy}ethyl 3,5 diaminobenzoate.
3-{4-[(1E)-3-(4-hexyloxyphenoxy)-3-oxoprop-1-enyl]phenoxy}propyl 3,5 diaminobenzoate.
5-{4-[(1E)-3-(4-hexyloxyphenoxy)-3-oxoprop-1-enyl]phenoxy}pentyl 3,5 diaminobenzoate.
7-{4-[(1E)-3-(4-hexyloxyphenoxy)-3-oxoprop-1-enyl]phenoxy}heptyl 3,5 diaminobenzoate.
8-{4-[(1E)-3-(4-hexyloxyphenoxy)-3-oxoprop-1-enyl]phenoxy}octyl 3,5 diaminobenzoate.
11-{4-[(1E)-3-(4-hexyloxyphenoxy)-3-oxoprop-1-enyl]phenoxy}undecyl 3,5 diaminobenzoate.
2-{4-[(1E)-3-(4-pentylcarbonyloxyphenoxy)-3-oxoprop-1-enyl]phenoxy}ethyl 3,5 diaminobenzoate.
3-{4-[(1E)-3-(4-pentylcarbonyloxyphenoxy)-3-oxoprop-1-enyl]phenoxy}propyl 3,5 diaminobenzoate.
5-{4-[(1E)-3-(4-pentylcarbonyloxyphenoxy)-3-oxoprop-1-enyl]phenoxy}pentyl 3,5 diaminobenzoate.
7-{4-[(1E)-3-(4-pentylcarbonyloxyphenoxy)-3-oxoprop-1-enyl]phenoxy}heptyl 3,5 diaminobenzoate.
8-{4-[(1E)-3-(4-pentylcarbonyloxyphenoxy)-3-oxoprop-1-enyl]phenoxy}octyl 3,5 diaminobenzoate.
11-{4-[(1E)-3-(4-pentylcarbonyloxyphenoxy)-3-oxoprop-1-enyl]phenoxy}undecyl 3,5 diaminobenzoate.
2-{4-[(1E)-3-(4-butylcarbonyloxyphenoxy)-3-oxoprop-1-enyl]phenoxy}ethyl 3,5 diaminobenzoate.
3-{4-[(1E)-3-(4-butylcarbonyloxyphenoxy)-3-oxoprop-1-enyl]phenoxy}propyl 3,5 diaminobenzoate.
5-{4-[(1E)-3-(4-butylcarbonyloxyphenoxy)-3-oxoprop-1-enyl]phenoxy}pentyl 3,5 diaminobenzoate.
7-{4-[(1E)-3-(4-butylcarbonyloxyphenoxy)-3-oxoprop-1-enyl]phenoxy}heptyl 3,5 diaminobenzoate.
8-{4-[(1E)-3-(4-butylcarbonyloxyphenoxy)-3-oxoprop-1-enyl]phenoxy}octyl 3,5 diaminobenzoate.
11-{4-[(1E)-3-(4-butylcarbonyloxyphenoxy)-3-oxoprop-1-enyl]phenoxy}undecyl 3,5 diaminobenzoate.
2-{4-[(1E)-3-(4-hexylcarbonyloxyphenoxy)-3-oxoprop-1-enyl]phenoxy}ethyl 3,5 diaminobenzoate.
3-{4-[(1E)-3-(4-hexylcarbonyloxyphenoxy)-3-oxoprop-1-enyl]phenoxy}propyl 3,5 diaminobenzoate.
5-{4-[(1E)-3-(4-hexylcarbonyloxyphenoxy)-3-oxoprop-1-enyl]phenoxy}pentyl 3,5 diaminobenzoate.
7-{4-[(1E)-3-(4-hexylcarbonyloxyphenoxy)-3-oxoprop-1-enyl]phenoxy}heptyl 3,5 diaminobenzoate.
8-{4-[(1E)-3-(4-hexylcarbonyloxyphenoxy)-3-oxoprop-1-enyl]phenoxy}octyl 3,5 diaminobenzoate.
11-{4-[(1E)-3-(4-hexylcarbonyloxyphenoxy)-3-oxoprop-1-enyl]phenoxy}undecyl 3,5 diaminobenzoate.
2-{4-[(1E)-3-(4-pentylphenoxy)-3-oxoprop-1-enyl]phenoxy}ethyl 3,5 diaminobenzoate.
3-{4-[(1E)-3-(4-pentylphenoxy)-3-oxoprop-1-enyl]phenoxy}propyl 3,5 diaminobenzoate.
5-{4-[(1E)-3-(4-pentylphenoxy)-3-oxoprop-1-enyl]phenoxy}pentyl 3,5 diaminobenzoate.
7-{4-[(1E)-3-(4-pentylphenoxy)-3-oxoprop-1-enyl]phenoxy}heptyl 3,5 diaminobenzoate.

8-{4-[(1E)-3-(4-pentylphenoxy)-3-oxoprop-1-enyl]phenoxy}octyl 3,5 diaminobenzoate.
11-{4-[(1E)-3-(4-pentylphenoxy)-3-oxoprop-1-enyl]phenoxy}undecyl 3,5 diaminobenzoate.
2-{4-[(1E)-3-(4-butylphenoxy)-3-oxoprop-1-enyl]phenoxy}ethyl 3,5 diaminobenzoate.
3-{4-[(1E)-3-(4-butylphenoxy)-3-oxoprop-1-enyl]phenoxy}propyl 3,5 diaminobenzoate.
5-{4-[(1E)-3-(4-butylphenoxy)-3-oxoprop-1-enyl]phenoxy}pentyl 3,5 diaminobenzoate.
7-{4-[(1E)-3-(4-butylphenoxy)-3-oxoprop-1-enyl]phenoxy}heptyl 3,5 diaminobenzoate.
8-{4-[(1E)-3-(4-butylphenoxy)-3-oxoprop-1-enyl]phenoxy}octyl 3,5 diaminobenzoate.
11-{4-[(1E)-3-(4-butylphenoxy)-3-oxoprop-1-enyl]phenoxy}undecyl 3,5 diaminobenzoate.
2-{4-[(1E)-3-(4-hexylphenoxy)-3-oxoprop-1-enyl]phenoxy}ethyl 3,5 diaminobenzoate.
3-{4-[(1E)-3-(4-hexylphenoxy)-3-oxoprop-1-enyl]phenoxy}propyl 3,5 diaminobenzoate.
5-{4-[(1E)-3-(4-hexylphenoxy)-3-oxoprop-1-enyl]phenoxy}pentyl 3,5 diaminobenzoate.
7-{4-[(1E)-3-(4-hexylphenoxy)-3-oxoprop-1-enyl]phenoxy}heptyl 3,5 diaminobenzoate.
8-{4-[(1E)-3-(4-hexylphenoxy)-3-oxoprop-1-enyl]phenoxy}octyl 3,5 diaminobenzoate.
11-{4-[(1E)-3-(4-hexylphenoxy)-3-oxoprop-1-enyl]phenoxy}undecyl 3,5 diaminobenzoate.
2-{4-[(1E)-3-(4-(4,4,4-trifluorobutyloxy)phenoxy)-3-oxoprop-1-enyl]phenoxy}ethyl 3,5 diaminobenzoate.
5-{4-[(1E)-3-(4-(4,4,4-trifluorobutyloxy)phenoxy)-3-oxoprop-1-enyl]phenoxy}pentyl 3,5 diaminobenzoate.
7-{4-[(1E)-3-(4-(4,4,4-trifluorobutyloxy)phenoxy)-3-oxoprop-1-enyl]phenoxy}heptyl 3,5 diaminobenzoate.
8-{4-[(1E)-3-(4-(4,4,4-trifluorobutyloxy)phenoxy)-3-oxoprop-1-enyl]phenoxy}octyl 3,5 diaminobenzoate.
11-{4-[(1E)-3-(4-(4,4,4-trifluorobutyloxy)phenoxy)-3-oxoprop-1-enyl]phenoxy}undecyl 3,5 diaminobenzoate.
2-{4-[(1E)-3-(4-cyclopentyloxyphenoxy)-3-oxoprop-1-enyl]phenoxy}ethyl 3,5 diaminobenzoate.
3-{4-[(1E)-3-(4-(3-methylpentyloxy)phenoxy)-3-oxoprop-1-enyl]phenoxy}propyl 3,5 diaminobenzoate.
5-{4-[(1E)-3-(4-[3-methoxy-1-pentyloxy]phenoxy)-3-oxoprop-1-enyl]phenoxy}pentyl 3,5 diaminobenzoate.
6-{4-[(1E)-3-(4-[3-methoxy-1-pentyloxy]phenoxy)-3-oxoprop-1-enyl]phenoxy}hexyl 3,5 diaminobenzoate
7-{4-[(1E)-3-(3-methoxy-4-pentyloxyphenoxy)-3-oxoprop-1-enyl]phenoxy}heptyl 3,5 diaminobenzoate.
8-{4-[(1E)-3-(2,3-difluoro-4-pentyloxyphenoxy)-3-oxoprop-1-enyl]phenoxy}octyl 3,5 diaminobenzoate.
11-{4-[(1E)-3-(4-(4-propylcyclohexyl)carbonyloxyphenoxy)-3-oxoprop-1-enyl]phenoxy}undecyl 3,5 diaminobenzoate.
2-{2-methoxy-4-[(1E)-3-(4-pentyloxyphenoxy)-3-oxoprop-1-enyl]phenoxy}ethyl 3,5 diaminobenzoate.
3-{2-methoxy-4-[(1E)-3-(4-pentyloxyphenoxy)-3-oxoprop-1-enyl]phenoxy}propyl 3,5 diaminobenzoate.
5-{2-methoxy-4-[(1E)-3-(4-pentyloxyphenoxy)-3-oxoprop-1-enyl]phenoxy}pentyl 3,5 diaminobenzoate.
6-{2-methoxy-4-[(1E)-3-(4-pentyloxyphenoxy)-3-oxoprop-1-enyl]phenoxy}hexyl 3,5 diaminobenzoate
6-{2-methoxy-4-[(1E)-3-(4-butyloxyphenoxy)-3-oxoprop-1-enyl]phenoxy}hexyl 3,5 diaminobenzoate.
7-{2-ethoxy-4-[(1E)-3-(4-pentyloxyphenoxy)-3-oxoprop-1-enyl]phenoxy}heptyl 3,5 diaminobenzoate.
8-{2-methoxy-4-[(1E)-3-(4-pentyloxyphenoxy)-3-oxoprop-1-enyl]phenoxy}octyl 3,5 diaminobenzoate.
11-{2-methoxy-4-[(1E)-3-(4-pentyloxyphenoxy)-3-oxoprop-1-enyl]phenoxy}undecyl 3,5 diaminobenzoate.
2-{4-[(1E)-3-(4-pentyloxyphenoxy)-3-oxoprop-1-enyl]phenylcarbonyloxy}ethyl 3,5 diaminobenzoate.
3-{4-[(1E)-3-(4-pentyloxyphenoxy)-3-oxoprop-1-enyl]phenylcarbonyloxy}propyl 3,5 diaminobenzoate.
5-{4-[(1E)-3-(4-pentyloxyphenoxy)-3-oxoprop-1-enyl]phenylcarbonyloxy}pentyl 3,5 diaminobenzoate.
7-{4-[(1E)-3-(4-pentyloxyphenoxy)-3-oxoprop-1-enyl]phenylcarbonyloxy}heptyl 3,5 diaminobenzoate.
8-{4-[(1E)-3-(4-pentyloxyphenoxy)-3-oxoprop-1-enyl]phenylcarbonyloxy}octyl 3,5 diaminobenzoate.
11-{4-[(1E)-3-(4-pentyloxyphenoxy)-3-oxoprop-1-enyl]phenylcarbonyloxy}undecyl 3,5 diaminobenzoate.
2-{4-[(1E)-3-(4-butyloxyphenoxy)-3-oxoprop-1-enyl]phenylcarbonyloxy}ethyl 3,5 diaminobenzoate.
3-{4-[(1E)-3-(4-butyloxyphenoxy)-3-oxoprop-1-enyl]phenylcarbonyloxy}propyl 3,5 diaminobenzoate.
5-{4-[(1E)-3-(4-butyloxyphenoxy)-3-oxoprop-1-enyl]phenylcarbonyloxy}pentyl 3,5 diaminobenzoate.
7-{4-[(1E)-3-(4-butyloxyphenoxy)-3-oxoprop-1-enyl]phenylcarbonyloxy}heptyl 3,5 diaminobenzoate.
8-{4-[(1E)-3-(4-butyloxyphenoxy)-3-oxoprop-1-enyl]phenylcarbonyloxy}octyl 3,5 diaminobenzoate.
11-{4-[(1E)-3-(4-butyloxyphenoxy)-3-oxoprop-1-enyl]phenylcarbonyloxy}undecyl 3,5 diaminobenzoate.
2-{4-[(1E)-3-(4-hexyloxyphenoxy)-3-oxoprop-1-enyl]phenylcarbonyloxy}ethyl 3,5 diaminobenzoate.
3-{4-[(1E)-3-(4-hexyloxyphenoxy)-3-oxoprop-1-enyl]phenylcarbonyloxy}propyl 3,5 diaminobenzoate.
5-{4-[(1E)-3-(4-hexyloxyphenoxy)-3-oxoprop-1-enyl]phenylcarbonyloxy}pentyl 3,5 diaminobenzoate.
7-{4-[(1E)-3-(4-hexyloxyphenoxy)-3-oxoprop-1-enyl]phenylcarbonyloxy}heptyl 3,5 diaminobenzoate.
8-{4-[(1E)-3-(4-hexyloxyphenoxy)-3-oxoprop-1-enyl]phenylcarbonyloxy}octyl 3,5 diaminobenzoate.
11-{4-[(1E)-3-(4-hexyloxyphenoxy)-3-oxoprop-1-enyl]phenylcarbonyloxy}undecyl 3,5 diaminobenzoate.
2-{4-[(1E)-3-(4-pentylcarbonyloxyphenoxy)-3-oxoprop-1-enyl]phenylcarbonyloxy}ethyl 3,5 diaminobenzoate.
3-{4-[(1E)-3-(4-pentylcarbonyloxyphenoxy)-3-oxoprop-1-enyl]phenylcarbonyloxy}propyl 3,5 diaminobenzoate.
5-{4-[(1E)-3-(4-pentylcarbonyloxyphenoxy)-3-oxoprop-1-enyl]phenylcarbonyloxy}pentyl 3,5 diaminobenzoate.
7-{4-[(1E)-3-(4-pentylcarbonyloxyphenoxy)-3-oxoprop-1-enyl]phenylcarbonyloxy}heptyl 3,5 diaminobenzoate.
8-{4-[(1E)-3-(4-pentylcarbonyloxyphenoxy)-3-oxoprop-1-enyl]phenylcarbonyloxy}octyl 3,5 diaminobenzoate.
11-{4-[(1E)-3-(4-pentylcarbonyloxyphenoxy)-3-oxoprop-1-enyl]phenylcarbonyloxy}undecyl 3,5 diaminobenzoate.
2-{4-[(1E)-3-(4-butylcarbonyloxyphenoxy)-3-oxoprop-1-enyl]phenylcarbonyloxy}ethyl 3,5 diaminobenzoate.
3-{4-[(1E)-3-(4-butylcarbonyloxyphenoxy)-3-oxoprop-1-enyl]phenylcarbonyloxy}propyl 3,5 diaminobenzoate.
5-{4-[(1E)-3-(4-butylcarbonyloxyphenoxy)-3-oxoprop-1-enyl]phenylcarbonyloxy}pentyl 3,5 diaminobenzoate.
7-{4-[(1E)-3-(4-butylcarbonyloxyphenoxy)-3-oxoprop-1-enyl]phenylcarbonyloxy}heptyl 3,5 diaminobenzoate.
8-{4-[(1E)-3-(4-butylcarbonyloxyphenoxy)-3-oxoprop-1-enyl]phenylcarbonyloxy}octyl 3,5 diaminobenzoate.
1-{4-[(1E)-3-(4-butylcarbonyloxyphenoxy)-3-oxoprop-1-enyl]phenylcarbonyloxy}undecyl 3,5 diaminobenzoate.
2-{4-[(1E)-3-(4-hexylcarbonyloxyphenoxy)-3-oxoprop-1-enyl]phenylcarbonyloxy}ethyl 3,5 diaminobenzoate.
3-{4-[(1E)-3-(4-hexylcarbonyloxyphenoxy)-3-oxoprop-1-enyl]phenylcarbonyloxy}propyl 3,5 diaminobenzoate.

5-{4-[(1E)-3-(4-hexylcarbonyloxyphenoxy)-3-oxoprop-1-enyl]phenylcarbonyloxy}pentyl 3,5 diaminobenzoate.
7-{4-[(1E)-3-(4-hexylcarbonyloxyphenoxy)-3-oxoprop-1-enyl]phenylcarbonyloxy}heptyl 3,5 diaminobenzoate.
8-{4-[(1E)-3-(4-hexylcarbonyloxyphenoxy)-3-oxoprop-1-enyl]phenylcarbonyloxy}octyl 3,5 diaminobenzoate.
11-{4-[(1E)-3-(4-hexylcarbonyloxyphenoxy)-3-oxoprop-1-enyl]phenylcarbonyloxy}undecyl 3,5 diaminobenzoate.
2-{4-[(1E)-3-(4-pentylphenoxy)-3-oxoprop-1-enyl]phenylcarbonyloxy}ethyl 3,5 diaminobenzoate.
3-{4-[(1E)-3-(4-pentylphenoxy)-3-oxoprop-1-enyl]phenylcarbonyloxy}propyl 3,5 diaminobenzoate.
5-{4-[(1E)-3-(4-pentylphenoxy)-3-oxoprop-1-enyl]phenylcarbonyloxy}pentyl 3,5 diaminobenzoate.
7-{4-[(1E)-3-(4-pentylphenoxy)-3-oxoprop-1-enyl]phenylcarbonyloxy}heptyl 3,5 diaminobenzoate.
8-{4-[(1E)-3-(4-pentylphenoxy)-3-oxoprop-1-enyl]phenylcarbonyloxy}octyl 3,5 diaminobenzoate.
11-{4-[(1E)-3-(4-pentylphenoxy)-3-oxoprop-1-enyl]phenylcarbonyloxy}undecyl 3,5 diaminobenzoate.
6-{4-[(1E)-3-(4-pentyloxyphenoxy)-3-oxoprop-1-enyl]phenoxycarbonyl}hexyl 3,5 diaminobenzoate.
6-{2-methoxy-4-[(1E)-3-[4-(4-cyclohexylphenoxy)butoxy]-3-oxoprop-1-enyl]phenoxy}hexyl 3,5 diaminobenzoate.
6-{4-[(1E)-3-[4-(4-cyclohexylphenoxy)butoxy]-3-oxoprop-1-enyl]phenoxy}hexyl 3,5 diaminobenzoate.
6-{4-[(1E)-3-(4-butyloxyphenoxy)-3-oxoprop-1-enyl]phenoxy}hexyl 3,5 diaminobenzoate,
5-{4-[(1E)-3-(4-pentyloxyphenoxy)-3-oxoprop-1-enyl]phenoxycarbonyl}pentyl 3,5 diaminobenzoate,
5-{4-[(1E)-3-(4-pentylphenoxy)-3-oxoprop-1-enyl]phenoxycarbonyl}pentyl 3,5 diaminobenzoate,
6-{4-[(1E)-3-(4-pentylphenoxy)-3-oxoprop-1-enyl]phenoxy}hexyl 3,5 diaminobenzoate.
2-{4-[(1E)-3-(4'-pentyl-1,1'-biphenyl-4-yl)-3-oxoprop-1-enyl]phenoxy}ethyl 3,5 diaminobenzoate.
3-{4-[(1E)-3-(4'-pentyl-1,1'-biphenyl-4-yl)-3-oxoprop-1-enyl]phenoxy}propyl 3,5 diaminobenzoate.
5-{4-[(1E)-3-(4'-pentyl-1,1'-biphenyl-4-yl)-3-oxoprop-1-enyl]phenoxy}pentyl 3,5 diaminobenzoate
6-{4-[(1E)-3-(4'-pentyl-1,1'-biphenyl-4-yl)-3-oxoprop-1-enyl]phenoxy}hexyl 3,5 diaminobenzoate
7-{4-[(1E)-3-(4'-pentyl-1,1'-biphenyl-4-yl)-3-oxoprop-1-enyl]phenoxy}heptyl 3,5 diaminobenzoate.
8-{4-[(1E)-3-(4'-pentyl-1,1'-biphenyl-4-yl)-3-oxoprop-1-enyl]phenoxy}octyl 3,5 diaminobenzoate.
11-{4-[(1E)-3-(4'-pentyl-1,1'-biphenyl-4-yl)-3-oxoprop-1-enyl]phenoxy}undecyl 3,5 diaminobenzoate.
2-{4-[(1E)-3-(4'-propyl-1,1'-biphenyl-4-yl)-3-oxoprop-1-enyl]phenoxy}ethyl 3,5 diaminobenzoate.
3-{4-[(1E)-3-(4'-propyl-1,1'-biphenyl-4-yl)-3-oxoprop-1-enyl]phenoxy}propyl 3,5 diaminobenzoate.
5-{4-[(1E)-3-(4'-propyl-1,1'-biphenyl-4-yl)-3-oxoprop-1-enyl]phenoxy}pentyl 3,5 diaminobenzoate
6-{4-[(1E)-3-(4'-propyl-1,1'-biphenyl-4-yl)-3-oxoprop-1-enyl]phenoxy}hexyl 3,5 diaminobenzoate
7-{4-[(1E)-3-(4'-propyl-1,1'-biphenyl-4-yl)-3-oxoprop-1-enyl]phenoxy}heptyl 3,5 diaminobenzoate.
8-{4-[(1E)-3-(4'-propyl-1,1'-biphenyl-4-yl)-3-oxoprop-1-enyl]phenoxy}octyl 3,5 diaminobenzoate.
11-{4-[(1E)-3-(4'-propyl-1,1'-biphenyl-4-yl)-3-oxoprop-1-enyl]phenoxy}undecyl 3,5 diaminobenzoate.
2-{4-[(1E)-3-(6-pentyloxy-2-naphtyloxy)-3-oxoprop-1-enyl]phenoxy}ethyl 3,5 diaminobenzoate.
3-{4-[(1E)-3-(6-pentyloxy-2-naphtyloxy)-3-oxoprop-1-enyl]phenoxy}propyl 3,5 diaminobenzoate.
5-{4-[(1E)-3-(6-pentyloxy-2-naphtyloxy)-3-oxoprop-1-enyl]phenoxy}pentyl 3,5 diaminobenzoate
6-{4-[(1E)-3-(6-pentyloxy-2-naphtyloxy)-3-oxoprop-1-enyl]phenoxy}hexyl 3,5 diaminobenzoate
7-{4-[(1E)-3-(6-pentyloxy-2-naphtyloxy)-3-oxoprop-1-enyl]phenoxy}heptyl 3,5 diaminobenzoate.
8-{4-[(1E)-3-(6-pentyloxy-2-naphtyloxy)-3-oxoprop-1-enyl]phenoxy}octyl 3,5 diaminobenzoate.
11-{4-[(1E)-3-(6-pentyloxy-2-naphtyloxy)-3-oxoprop-1-enyl]phenoxy}undecyl 3,5 diaminobenzoate.
2-{4-[(1E)-3-(4-cyclohexylphenoxy)-3-oxoprop-1-enyl]phenoxy}ethyl 3,5 diaminobenzoate.
3-{4-[(1E)-3-(4-cyclohexylphenoxy)-3-oxoprop-1-enyl]phenoxy}propyl 3,5 diaminobenzoate.
5-{4-[(1E)-3-(4-cyclohexylphenoxy)-3-oxoprop-1-enyl]phenoxy}pentyl 3,5 diaminobenzoate
6-{4-[(1E)-3-(4-cyclohexylphenoxy)-3-oxoprop-1-enyl]phenoxy}hexyl 3,5 diaminobenzoate
7-{4-[(1E)-3-(4-cyclohexylphenoxy)-3-oxoprop-1-enyl]phenoxy}heptyl 3,5 diaminobenzoate.
8-{4-[(1E)-3-(4-cyclohexylphenoxy)-3-oxoprop-1-enyl]phenoxy}octyl 3,5 diaminobenzoate.
11-{4-[(1E)-3-(4-cyclohexylphenoxy)-3-oxoprop-1-enyl]phenoxy}undecyl 3,5 diaminobenzoate.

EXAMPLE 2

Polymerisation Step A (Formation of the Polyamic Acid)

630 mg (3.210 mmol) of 1,2,3,4-cyclobutanetetracarboxylic acid dianhydride were added to a solution of 2.000 g (3.570 mmol) of 6-{4-[(1E)-3-(4-pentyloxyphenoxy)-3-oxoprop-1-enyl]phenoxy}hexyl 3,5 diaminobenzoate (EXAMPLE 1) in 14.0 ml of tetrahydrofuran (THF). Stirring was then carried out at 0° C. for 2 h. Then another 0.070 mg (0.357 mmol) of 1,2,3,4-cyclobutantetracarboxylic acid dianhydride were added. The mixture was subsequently allowed to react for 21 h at room temperature. The polymer mixture was diluted with 14 ml THF, precipitated into 800 ml diethyl ether and collected by filtration. The polymer was reprecipitated form THF (40 ml) into 1400 ml water to yield, after drying at room temperature under vacuum, 2.35 g of Polyamic Acid No. 1 in the form of a white powder; [η]=0.71 dL/g.

EXAMPLE 3

Polymerisation Step B (Formation of the Polyimide)

0.50 g of Polyamic Acid No. 1 obtained in above EXAMPLE 2 were dissolved in 3 ml of 1-methyl-2-pyrrolidon (NMP). Thereto were added 0.28 g (3.57 mmol) of pyridine and 364 mg (3.57 mmol) acetic acid anhydride, and the dehydration and ring closure was carried out at 80° C. for 2 h. The polymer mixture was diluted with 1.5 ml NMP, precipitated into 100 ml diethyl ether and collected by filtration. The polymer was reprecipitated from THF (10 ml) into 200 ml water to yield, after drying at room temperature under vacuum, 0.55 g Polyimide No 1; [η]=0.30 dL/g.

EXAMPLE 4

Synthesis

Preparation of bis[6-{4-[(1E)-3-(4-pentyloxyphenoxy)-3-oxoprop-1-enyl]phenoxy}hexyl]2,2-bis(aminobenzyl)malonate

4.1 Dimethyl bis(4-nitrobenzyl)malonate

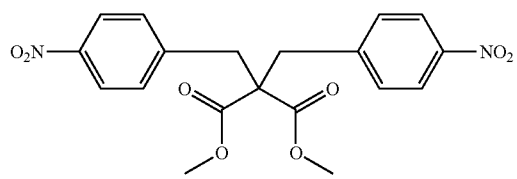

16.25 g (0.123 mol) of dimethyl malonate were dissolved in 500 ml tetrahydrofurane. A suspension of 10.74 g (0.246 mol) sodium hydride 55% dispersion in mineral oil and 20 ml tetrahydrofurane were added at 0° C. in 1 h. After 0.5 h, a mixture of 53.2 g (0.246 mol) 4-nitrobenzyl bromide and 200 ml tetrahydrofurane was added dropwise. After 18.5 h at room temperature, the reaction mixture was added to water. The product was collected by filtration and washed with a lot of water to yield 52.8 g of dimethyl bis(4-nitrobenzyl)malonate as yellowish powder. The product was used without further purification.

4.2 Bis[6-chlorohexyl]2,2 bis(4-nitrobenzyl)malonate

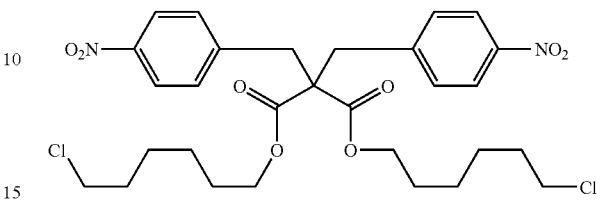

26.1 g (0.065 mol) dimethyl bis(4-nitrobenzyl)malonate, 84 g (0.61 mol) 6-chlorohexanol, 23.0 g (0.10 mol) tetraethyl orthotitanate were suspended in 50 ml toluene. The reaction mixture was subsequently allowed to react for 72 h at refluxing temperature. The reaction mixture was partitioned between water and ethyl acetate; the organic phase was washed repeatedly with water, dried over magnesium sulphate, filtered and concentrated by rotary evaporation. The product was precipitated with 200 ml cyclohexane, collected by filtration and washed with hexane to yield 27.6 g of bis[6-chlorohexyl]2,2 bis(4-nitrobenzyl)malonate as beige powder.

4.3 Bis[6-{4-[(1E)-3-(4-pentyloxyphenoxy)-3-oxoprop-1-enyl]phenoxy}hexyl]2,2 bis(4-nitrobenzyl)malonate

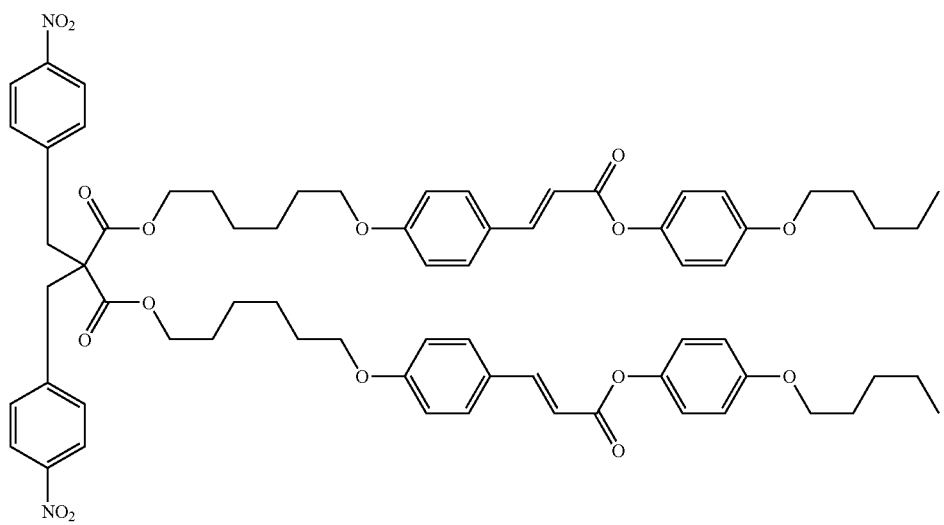

2.80 g (4.6 mmol) bis[6-chlorohexyl]2,2 bis(4-nitrobenzyl)malonate, 3.0 g (9.2 mmol) 4-pentoxyphenyl (2E)-3-{4-hydroxyphenyl}acrylate and 0.17 g (0.46 mmol) tetrabutylammonium iodide were dissolved in 30 ml 2-butanone. 2.53 g (18.3 mmol) potassium carbonate were added. The resulting suspension was heated at refluxing temperature and allowed to react for 48 h. After cooling to room temperature, the reaction mixture was partitioned between ethyl acetate and water. The organic phase was washed repeatedly with water, dried over sodium sulfate, filtered and concentrated by rotary evaporation to yield 3.6 g bis[6-{4-[(1E)-3-(4-pentyloxyphenoxy)-3-oxoprop-1-enyl]phenoxy}hexyl]2,2 bis(4-nitrobenzyl)malonate.

4.4. Bis[6-{4-[(1E)-3-(4-pentyloxyphenoxy)-3-oxoprop-1-enyl]phenoxy}hexyl]2,2 bis(4-aminobenzyl)malonate The Following Diamines were Synthesized in an Analogous Manner:

bis[4-{4-[(1E)-3-(4-pentyloxyphenoxy)-3-oxoprop-1-enyl]phenoxy}butyl]2,2 bis(4-aminobenzyl)malonate.
bis[11-{4-[(1E)-3-(4-pentyloxyphenoxy)-3-oxoprop-1-enyl]phenoxy}undecyl]2,2 bis(4-aminobenzyl)malonate.
bis[4-{4-[(1E)-3-(4-hexyloxyphenoxy)-3-oxoprop-1-enyl]phenoxy}butyl]2,2 bis(4-aminobenzyl)malonate.
bis[6-{4-[(1E)-3-(4-hexyloxyphenoxy)-3-oxoprop-1-enyl]phenoxy}hexyl]2,2 bis(4-aminobenzyl)malonate.
bis[4-{4-[(1E)-3-(4-butylphenoxy)-3-oxoprop-1-enyl]phenoxy}butyl]2,2 bis(4-aminobenzyl)malonate.
bis[6-{4-[(1E)-3-(4-butylphenoxy)-3-oxoprop-1-enyl]phenoxy}hexyl]2,2 bis(4-aminobenzyl)malonate.
bis[4-{4-[(1E)-3-(4-butyloxyphenoxy)-3-oxoprop-1-enyl]phenoxy}butyl]2,2 bis(4-aminobenzyl)malonate.

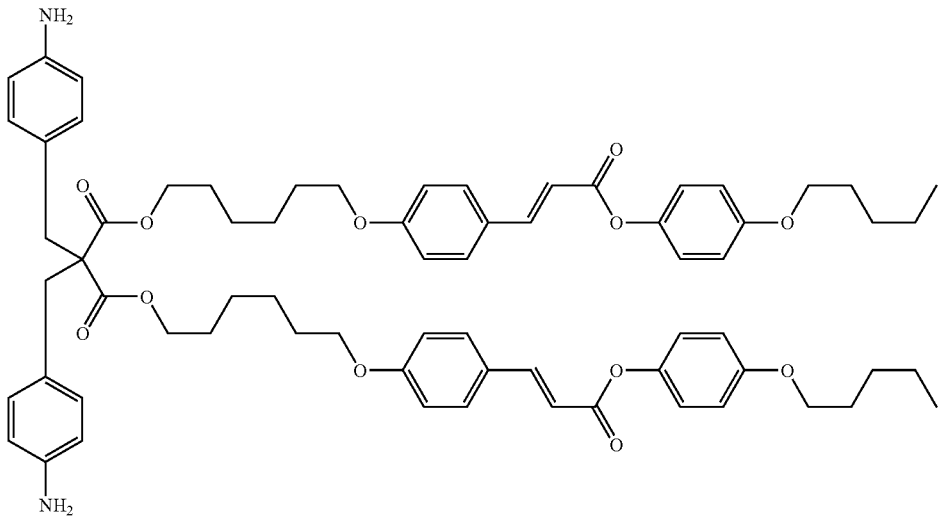

1.54 g (1.36 mmol) bis[6-{4-[(1E)-3-(4-pentyloxyphenoxy)-3-oxoprop-1-enyl]phenoxy}hexyl]2,2 bis(4-nitrobenzyl)malonate. were dissolved in a mixture of 25 ml N,N-dimethylformamide and 2.8 ml water. 2.21 g (8.18 mmol) ferric chloride hexahydrate and 0.716 g (10.95 mmol) zinc powder were added. The mixture was allowed to react for 1 h. The reaction mixture was then partitioned between ethyl acetate and water and filtered. The organic phase was washed repeatedly with water, dried over sodium sulfate, filtered and concentrated by rotary evaporation to yield 1.1 g bis[6-{4-[(1E)-3-(4-pentyloxyphenoxy)-3-oxoprop-1-enyl]phenoxy}hexyl]2,2 bis(4-aminobenzyl)malonate.

bis[8-{4-[(1E)-3-(4-butyloxyphenoxy)-3-oxoprop-1-enyl]phenoxy}octyl]2,2 bis(4-aminobenzyl)malonate.
bis[11-{4-[(1E)-3-(4-butyloxyphenoxy)-3-oxoprop-1-enyl]phenoxy}undecyl]2,2 bis(4-aminobenzyl)malonate.

EXAMPLE 5

5.1 Analogously to EXAMPLE 1, 6-{2-methoxy-4-[(1E)-3-(4-butyloxyphenoxy)-3-oxoprop-1-enyl]phenoxy}hexyl 3,5 diaminobenzoate was synthesized.

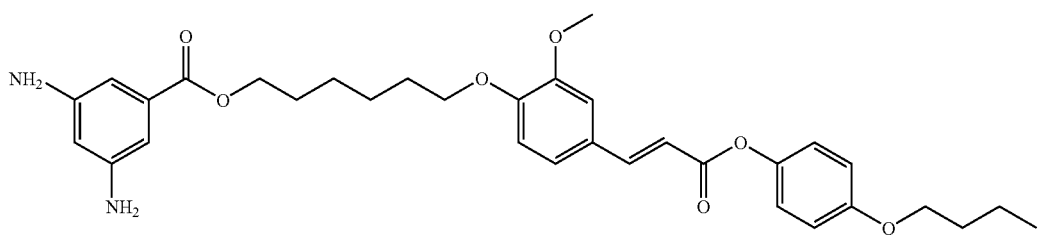

5.2 Analogously to EXAMPLE 2, the preparation of the Polyamic Acid was carried out using 1.500 g (2.601 mmol) 6-{2-methoxy-4-[(1E)-3-(4-butyloxyphenoxy)-3-oxoprop-1-enyl]phenoxy}hexyl 3,5 diaminobenzoate, and 510.11 mg (2.601 mmol) 1,2,3,4-cyclobutantetracarboxylic acid dianhydride to yield 0.56 g Polyamic Acid No. 2; [η]=0.72 dL/g.

EXAMPLE 6

6.1 Analogously to EXAMPLE 1, 6-{2-methoxy-4-[(1E)-3-(4-pentyloxyphenoxy)-3-oxoprop-1-enyl]phenoxy}hexyl 3,5 diaminobenzoate was synthesized.

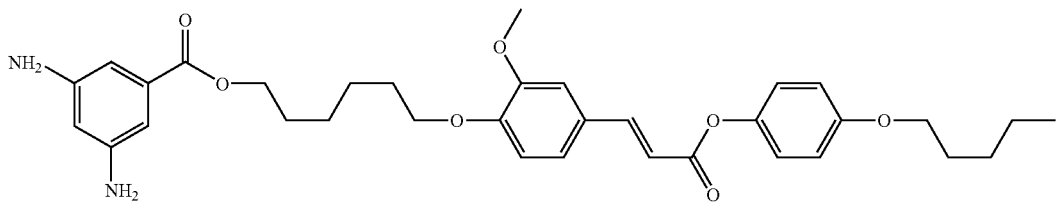

6.2 Analogously to EXAMPLE 2, the preparation of the Polyamic Acid was carried out using 1.722 mg (3.000 mmol) 6-{2-methoxy-4-[(1E)-3-(4-pentyloxyphenoxy)-3-oxoprop-1-enyl]phenoxy}hexyl 3,5 diaminobenzoate, and 88.3 mg (3.000 mmol) 1,2,3,4-cyclobutantetracarboxylic acid dianhydride to yield 0.56 g Polyamic Acid No. 3; [η]=2.05 dL/g.

EXAMPLE 7

7.1 Analogously to EXAMPLE 1, 6-{4-[(1E)-3-(4-butyloxyphenoxy)-3-oxoprop-1-enyl]phenoxy}hexyl 3,5 diaminobenzoate was synthesized.

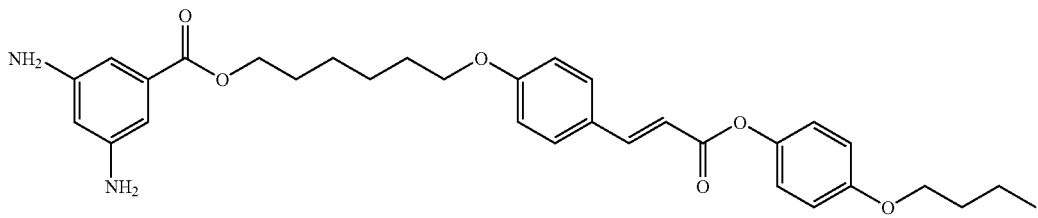

7.2 Analogously to EXAMPLE 2, the preparation of the Polyamic Acid was carried out using 1.328 g (2.429 mmol) 6-{4-[(1E)-3-(4-butyloxyphenoxy)-3-oxoprop-1-enyl] phenoxy}hexyl 3,5 diaminobenzoate, and 0.477 g (2.429 mmol) 1,2,3,4-cyclobutantetracarboxylic acid dianhydride to yield 1.65 g Polyamic Acid No. 4; [η]=0.81 dL/g.

EXAMPLE 8

8.1 Analogously to EXAMPLE 1, 5-{4-[(1E)-3-(4-pentyloxyphenoxy)-3-oxoprop-1-enyl]phenoxycarbonyl}pentyl 3,5 diaminobenzoate was synthesized.

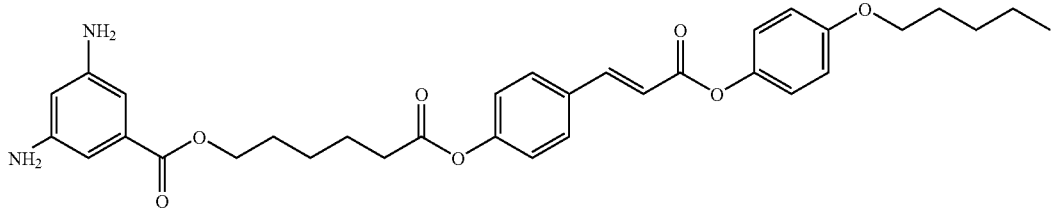

8.2 Analogously to EXAMPLE 2, the preparation of the Polyamic Acid was carried out using 700.0 mg (1.2181 mmol) 5-{4-[(1E)-3-(4-pentyloxyphenoxy)-3-oxoprop-1-enyl]phenoxycarbonyl}pentyl 3,5 diaminobenzoate, 238.9 mg (1.2181 mmol) 1,2,3,4-cyclobutantetracarboxylic acid dianhydride to yield 0.90 g Polyamic Acid No. 5 [η]=0.73 dL/g.

EXAMPLE 9

9.1 Analogously to EXAMPLE 1, 5-{4-[(1E)-3-(4-pentylphenoxy)-3-oxoprop-1-enyl]phenoxycarbonyl}pentyl 3,5 diaminobenzoate was synthesized.

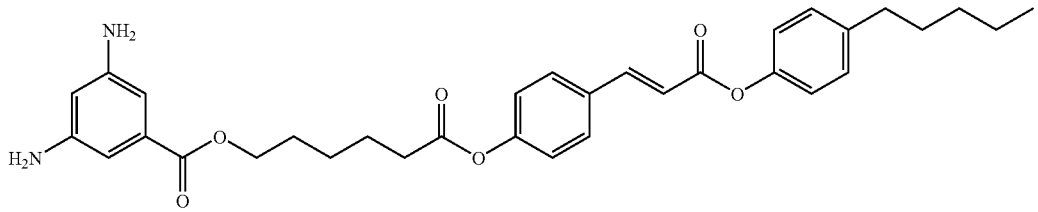

9.2 Analogously to EXAMPLE 2, the preparation of the Polyamic Acid was carried out using 744.7 mg (1.333 mmol) 5-{4-[(1E)-3-(4-pentylphenoxy)-3-oxoprop-1-enyl] phenoxycarbonyl}pentyl 3,5 diaminobenzoate, 261.4 mg (1.333 mmol) 1,2,3,4-cyclobutantetracarboxylic acid dianhydride to yield 0.93 g Polyamic Acid No. 6; [η]=0.74 dL/g.

EXAMPLE 10

10.1 Analogously to EXAMPLE 1, 6-{4-[(1E)-3-(4-pentylphenoxy)-3-oxoprop-1-enyl]phenoxy}hexyl 3,5 diaminobenzoate was synthesized.

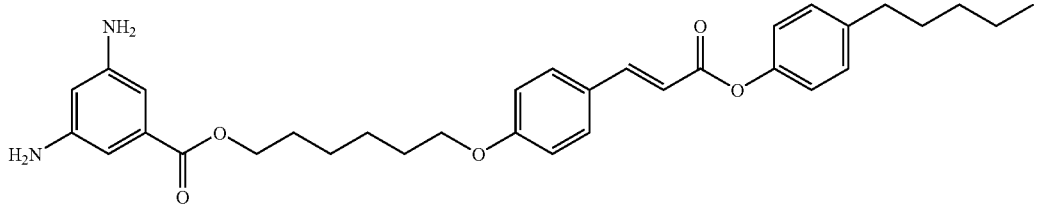

10.2 Analogously to EXAMPLE 2, the preparation of the Polyamic Acid was carried out using 1.000 g (1.836 mmol) 6-{4-[(1E)-3-(4-pentylphenoxy)3-oxoprop-1-enyl] phenoxy}hexyl 3,5 diaminobenzoate, 168.3 mg (1.836 mmol) 1,2,3,4-cyclobutantetracarboxylic acid dianhydride to yield 1.27 g Polyamic Acid No. 7; [η]=0.47 dL/g.

EXAMPLE 11

11.1 Analogously to EXAMPLE 1, 6-{4-[(1E)-3-[4-(4-cyclohexylphenoxy)butoxy]-3-oxoprop-1-enyl]phenoxy}hexyl 3,5 diaminobenzoate was synthesized.

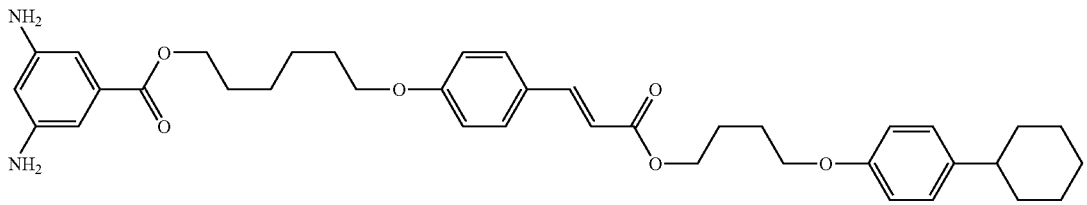

11.2 Analogously to EXAMPLE 2, the preparation of the Polyamic Acid was carried out using 0.500 g (0.7952 mmol) 6-{4-[(1E)-3-[4-(4-cyclohexylphenoxy)butoxy]-3-oxoprop-1-enyl]phenoxy}hexyl 3,5 diaminobenzoate, 144.9 mg (0.7952 mmol) 1,2,3,4-cyclobutantetracarboxylic acid dianhydride to yield 0.62 g Polyamic Acid No. 8; [η]=1.18 dL/g.

11.3 Analogously to EXAMPLE 2, the preparation of the Copolyamic Acid was carried out using 0.450 mg (0.7156 mmol) of 6-{4-[(1E)-3-[4-(4-cyclohexylphenoxy)butoxy]-3-oxoprop-1-enyl]phenoxyhexyl 3,5 diaminobenzoate, 73.80 mg (0.1789 mmol) of 6-{4-[(1E)-3-methoxy-3-oxoprop-1-enyl]phenoxy}hexyl 3,5 diaminobenzoate and 175.4 mg (0.8945 mmol) 1,2,3,4-cyclobutantetracarboxylic acid dianhydride to yield 0.65 g Copolyamic Acid No. 1; [η]=0.81 dL/g.

11.4 Analogously to EXAMPLE 2, the preparation of the Copolyamic Acid was carried out using 0.500 mg (0.7952 mmol) of 6-{4-[(1E)-3-[4-(4-cyclohexylphenoxy)butoxy]-3-oxoprop-1-enyl]phenoxyhexyl 3,5 diaminobenzoate, 21.50 mg (0.1988 mmol) 1,3-phenylendiamine and 194.5 mg (0.9938 mmol) 1,2,3,4-cyclobutantetracarboxylic acid dianhydride to yield 0.57 g Copolyamic Acid No. 2; [η]=0.28 dL/g.

EXAMPLE 12

12.1 Analogously to EXAMPLE 1, 6-{2-methoxy-4-[(1E)-3-[4-(4-cyclohexylphenoxy)butoxy]-3-oxoprop-1-enyl]phenoxy}hexyl 3,5 diaminobenzoate was synthesized.

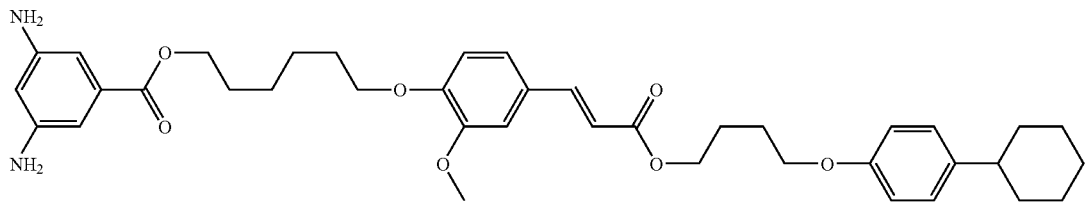

12.2 Analogously to EXAMPLE 2, the preparation of the Polyamic Acid was carried out using 0.5138 mg (0.7799 mmol) 6-{2-methoxy-4-[(1E)-3-[4-(4-cyclohexylphenoxy)butoxy]-3-oxoprop-1-enyl]phenoxy}hexyl 3,5 diaminobenzoate, 152.9 mg (0.7799 mmol) 1,2,3,4-cyclobutantetracarboxylic acid dianhydride to yield 0.65 g Polyamic Acid No. 9; [η]=1.09 dL/g.

EXAMPLE 13

13.1 Analogously to EXAMPLE 1, 6-{4-[(1E)-3-[4-(4-cyclohexylphenoxy)butoxy]-3-oxoprop-1-enyl]phenoxy}hexyl 3,5 diaminobenzoate was synthesized.

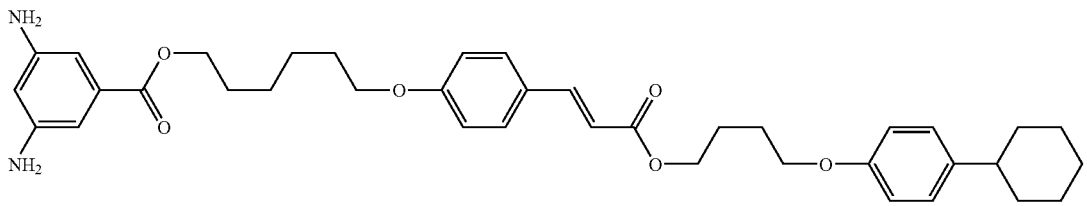

13.2 Analogously to EXAMPLE 2, the preparation of the Copolyamic Acid was carried out using 0.500 g (0.7952 mmol) 6-{4-[(1E)-3-[4-(4-cyclohexylphenoxy)butoxy]-3-oxoprop-1-enyl]phenoxy}hexyl 3,5 diaminobenzoate, 21.5 mg (0.1988 mmol) 1,3-phenylendiamine and 194.9 mg (0.9938 mmol), 1,2,3,4-cyclobutantetracarboxylic acid dianhydride to yield 0.62 g Copolyamic Acid No. 3; [η]=0.28 dL/g.

EXAMPLE 14

14.1 Analogously to EXAMPLE 1, 6-{4-[(1E)-3-(4-butyloxyphenoxy)-3-oxoprop-1-enyl]phenylcarbonyloxy}hexyl 3,5 diaminobenzoate was synthesized.

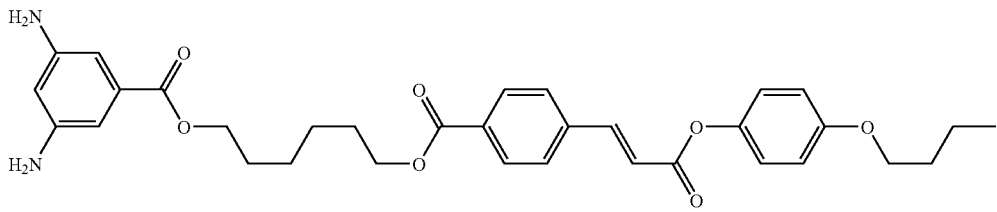

14.2 Analogously to EXAMPLE 2, the preparation of the Polyamic Acid was carried out using 433.5 mg (0.754 mmol) of 6-{4-[(1E)-3-(4-butyloxyphenoxy)-3-oxoprop-1-enyl]phenylcarbonyloxy}hexyl 3,5 diaminobenzoate and 335.1 mg (0.754 mmol) of 4,4'-(hexafluoroisopropylidene)diphthalic acid dianhydride to yield, after drying at room temperature under vacuum, 0.499 g of Polyamic Acid No. 10 in the from of a white powder; [η]=0.37 dL/g.

EXAMPLE 15

15.1 Analogously to EXAMPLE 1, 5-{4-[(1E)-3-(4-pentyloxyphenoxy)-3-oxoprop-1-enyl]phenyloxycarbonyl}pentyl 3,5 diaminobenzoate was synthesized.

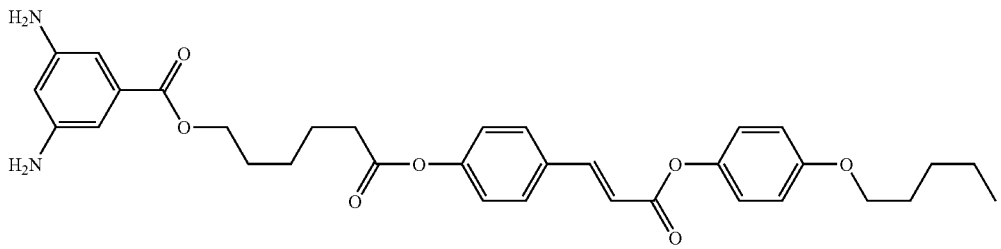

15.2 Analogously to EXAMPLE 2, the preparation of the Polyamic Acid was carried out using 1.000 g (1.740 mmol) of 5-{4-[(1E)-3-(4-pentyloxyphenoxy)-3-oxoprop-1-enyl]phenyloxycarbonyl}pentyl 3,5 diaminobenzoate, 512.0 mg (1.705 mmol) 4-(2,5-dioxotetrahydrofuran-3-yl)tetrahydronaphthalene-1,2-dicarboxylicacid dianhydride to yield 0.81 g Polyamic Acid No. 11; [η]=0.17 dL/g.

EXAMPLE 16

16.1 Analogously to EXAMPLE 1, 5-{4-[(1E)-3-(4-pentylphenoxy)-3-oxoprop-1-enyl]phenyloxycarbonyl}pentyl 3,5 diaminobenzoate was synthesized.

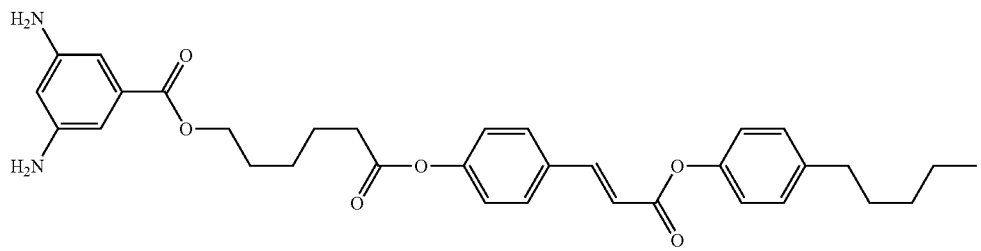

16.2 Analogously to EXAMPLE 2, the preparation of the Polyamic Acid was carried out using 1.000 g (1.790 mmol) of 5-{4-[(1E)-3-(4-pentylphenoxy)-3-oxoprop-1-enyl]phenyloxycarbonyl}pentyl 3,5 diaminobenzoate, 393.2 mg (1.754 mmol) 2,3,5-tricarboxycyclopentylacetic acid dianhydride to yield 0.71 g Polyamic Acid No. 12; [η]=0.38 dL/g.

EXAMPLE 17

17.1 Analogously to EXAMPLE 1, 6-{4-[(1E)-3-(1,1'-biphenyl-4-yloxy)butoxy]-3-oxoprop-1-enyl}phenoxy}hexyl 3,5 diaminobenzoate was synthesized.

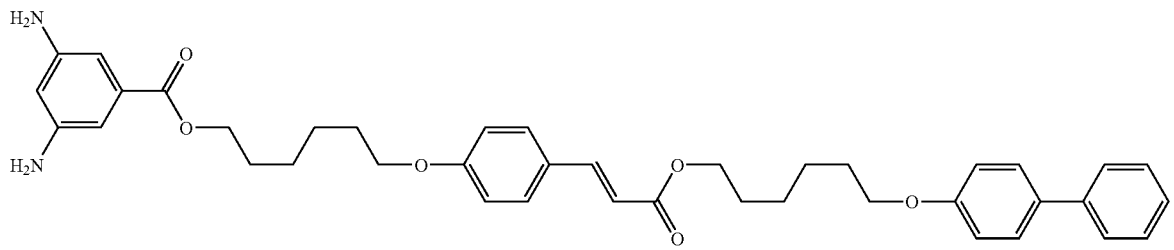

17.2 Analogously to EXAMPLE 2, the preparation of the Polyamic Acid was carried out using 0.500 mg (0.8029 mmol) of 6-{4-[(1E)-3-(1,1'-biphenyl-4-yloxy)butoxy]-3-oxoprop-1-enyl}phenoxy}hexyl 3,5 diaminobenzoate, 157.5 mg (0.8029 mmol) 1,2,3,4-cyclobutantetracarboxylic acid dianhydride to yield 0.62 g Polyamic Acid No. 13; [η]=0.66 dL/g.

EXAMPLE 18

18.1 Analogously to EXAMPLE 1, {4-[(1E)-3-(4-butyloxyphenoxy)-3-oxoprop-1-enyl]phenylcarbonyloxy}methyl 3,5 diaminobenzyl was synthesized.

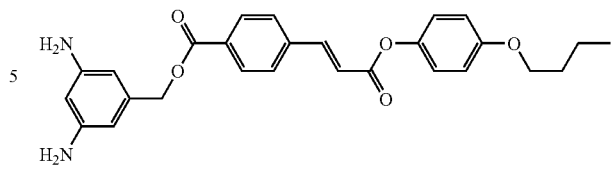

18.2 Analogously to EXAMPLE 2, the preparation of the Polyamic Acid was carried out using 0.660 mg (1.401 mmol) of {4-[(1E)-3-(4-butyloxyphenoxy)-3-oxoprop-1-enyl]phenylcarbonyloxy}methyl 3,5 diaminobenzyl, 274.78 mg (1.401 mmol) 1,2,3,4-cyclobutantetracarboxylic acid dianhydride to yield 0.81 g Polyamic Acid No. 14; [η]=0.48 dL/g.

For Comparative Evaluations Polyamic Acids were Produced Using Diamines Covered by the Above Cited Prior Art and Described Hereinafter:

COMPARATIVE EXAMPLE 1

Vertical Alignment

Polymerisation Step A (Formation of the Polyamic Acid)

The preparation was carried out analogously to EXAMPLE 2 using 500.0 mg (0.858 mmol) 6-{2-methoxy-4-[(1E)-3-undecyloxy-3-oxoprop-1-enyl]phenoxy}hexyl 3,5-diaminobenzoate, 168.3 mg (0.858 mmol) 1,2,3,4-cyclobutantetracarboxylic acid dianhydride to yield 0.56 g Comparative Polyamic Acid No 1; [η]=0.73 dL/g.

COMPARATIVE EXAMPLE 2

Planar Alignment

Polymerisation Step A (Formation of the Polyamic Acid)

The preparation was carried out analogously to EXAMPLE 2 using 501.3 mg (1.1328 mmol) 6-{2-methoxy-4-[(1E)-3-methoxy-3-oxoprop-1-enyl]phenoxy}hexyl 3,5-diaminobenzoate, 222.2 mg (1.1328 mmol) 1,2,3,4 cyclobu tantetracarboxylic acid dianhydride to yield 0.61 g Comparative Polyamic Acid No. 2; [η]=0.84 dL/g.

COMPARATIVE EXAMPLE 3

Vertical Alignment

Polymerisation Step A (Formation of the Polyamic Acid)

The preparation was carried out analogously to EXAMPLE 2 using 500.0 mg (0.849 mmol) 6-[((2E)-3-{4-[(4-pentyloxybenzoyl)oxy]phenyl}prop-2-enoyl)oxy]hexyl 3,5-diaminobenzoate, 166.6 mg (0.849 mmol) 1,2,3,4-cyclobutantetracarboxylic acid dianhydride to yield 0.52 g Comparative Polyamic Acid No 3; [η]=0.31 dL/g.

COMPARATIVE EXAMPLE 4

Planar Alignment

Polymerisation Step A (Formation of the Polyamic Acid)

The preparation was carried out analogously to EXAMPLE 2 using 2.000 g (3.653 mmol) 6-[((2E)-3-{4-[(4-methoxybenzoyl)oxy]phenyl}prop-2-enoyl)oxy]hexyl 3,5-diaminobenzoate, 716.5 mg (3.653 mmol) 1,2,3,4-cyclobutantetracarboxylic acid dianhydride to yield 2.55 g Comparative Polyamic Acid No. 4; [η]=0.33 dL/g.

EXAMPLE 19

Example for the Production of an Orientation Layer having a Defined Tilt Angle

A 2% solution of Polyamic Acid No. 1 (EXAMPLE 2) in cyclopentanone was filtered over a 0.2 µm Teflon filter and applied to a glass plate, which had been coated with indium-tin oxide (ITO), in a spin-coating apparatus at 3000 rev/min in the course of 60 seconds. The resulting film was then predried for 15 minutes at 130° C. and then imidized for 1 h at 200° C. to form a polyimide film. The so obtained LPP film was irradiated with linearly polarised UV light (30 mJ/cm$^2$), the direction of incidence of the light being inclined by 20° to 40° relative to the plate normal. The direction of polarisation of the light was kept in the plane defined by the direction of incidence of the light and the plate normal. From both plates a cell of 20 µm spacing was built such that the illuminated surfaces were facing each other and the previous polarisation directions of illumination were parallel. The cell was then filled with liquid crystal mixture MLC6609 from Merck in the isotropic phase at 100° C. The cell was then gradually cooled to room temperature at a rate ranging from 0.1° C./min to 2° C./min. Between crossed polarisers a uniformly oriented liquid crystal layer was observed. The tilt angle of this parallel cell, by crystal rotation method, was 88.5°.

EXAMPLE 20

Determination of the Tilt Angle's Photo-Stability

An orientation layer having a defined angle of tilt of 88.5°, as provided in aforementioned EXAMPLE 19, has been subjected to photo-stability experiments using a HANAU SUNTESTER apparatus. The light impact on the sample had a cut-off at 400 nm and an irradiance of 60 mW/cm$^2$. The angle of tilt remained stable over a time period of 800 h.

EXAMPLE 21

Determination of the Voltage Holding Ratio (VHR)

Two glass plates coated in accordance with above Example 19 were irradiated perpendicularly during 4 minutes with linearly polarised UV light. From both plates a cell of 10 µm spacing was built such that the illuminated surfaces were facing each other and the previous polarisation directions of illumination were parallel. This cell was then maintained at 120° C. under high vacuum for 14 h and thereafter filled with TFT liquid crystal mixture MLC6610 from Merck in vacuum at room temperature. Between crossed polarisers a uniformly oriented liquid crystal layer was observed. Prior to testing the voltage holding ratio (VHR) the cell was first subjected to ageing for 50 h at 120° C. The voltage decay V (at T=20 ms) of a voltage surge of 64 µs with $V_0$ (V at t=0)=0.2V was then measured over a period of T=20 ms. The voltage holding ratio then determined, given by VHR=$V_{rms}$(t=T)/$V_0$, was 96% at room temperature and 92% at 80° C.

EXAMPLE 22

Comparative Example A for the Production of an Orientation Layer Having a Defined Tilt Angle Two glass plates coated with Comparative Polyamic Acid No. 1 (same procedure as used in EXAMPLE 19) were irradiated with linearly polarised UV light (90 mJ/cm$^2$), the direction of incidence of the light being inclined by 40° relative to the plate normal. The direction of polarisation of the light was kept in the plane defined by the direction of incidence of the light and the plate normal. From both plates a cell of 20 µm spacing was built such that the illuminated surfaces were facing each other and the previous polarisation directions of illumination were parallel. The cell was then filled with liquid crystal mixture MLC6609 from Merck in the isotropic phase at 100° C. The cell was then gradually cooled to room temperature at a rate ranging from 0.1° C./min to 2° C./min. Between crossed polarisers a uniformly oriented liquid crystal layer was observed. The tilt angle of this parallel cell, by crystal rotation method, was 89°.

EXAMPLE 23

Comparative Example A for the Determination of the Voltage Holding Ratio (VHR)

Two glass plates coated with Comparative Polyamic Acid No 1 (same procedure as used in EXAMPLE 19) were irradiated perpendicularly during 4 minutes with linearly polarised UV light. From both plates a cell of 10 µm spacing was built such that the illuminated surfaces were facing each other and the previous polarisation directions of illumination were parallel. This cell was then maintained at 120° C. under high vacuum for 14 h and thereafter filled with TFT liquid crystal mixture MLC6610 from Merck in vacuum at room temperature. Between crossed polarisers a uniformly oriented liquid crystal layer was observed. Prior to testing the voltage holding ratio (VHR) the cell was first subjected to ageing for 50 h at 120° C. The voltage decay V (at T=20 ms) of a voltage surge of 64 µs with $V_0$ (V at t=0)=0.2V was then measured over a period of T=20 ms. The voltage holding ratio then determined, given by VHR=$V_{rms}$(t=T)/$V_0$, was 96% at room temperature and 77% at 80° C.

EXAMPLE 24

Comparative Example A for the Determination of the Tilt Angle's Photo-Stability

An orientation layer having a defined angle of tilt in accordance with EXAMPLE 22 has been subjected to photo-stability experiments using a HANAU SUNTESTER apparatus. The light impact on the sample had a cut-off at 400 nm and an irradiance of 60 mW/cm$^2$. The above angle of tilt was not stable over a time period of 800 h.

EXAMPLE 25

Comparative Example B for the Production of an Orientation Layer Having a Defined Tilt Angle Two glass plates coated with Comparative Polyamic Acid No. 2 (same procedure as used in EXAMPLE 19) irradiated with linearly polarised UV light (90 mJ/cm$^2$), the direction of incidence of the light being inclined by 40° relative to the plate normal. The direction of polarisation of the light was kept in the plane defined by the direction of incidence of the light and the plate normal. From both plates a cell of 20 μm spacing was built such that the illuminated surfaces were facing each other and the previous polarisation directions of illumination were parallel. The cell was then filled with liquid crystal mixture MLC6609 from Merck in the isotropic phase at 100° C. The cell was then gradually cooled to room temperature at a rate ranging from 0.1° C./min to 2° C./min. Between crossed polarisers a uniformly oriented liquid crystal layer was observed. The tilt angle of this parallel cell, by crystal rotation method, was 0°.

EXAMPLE 26

Comparative Example B for the Determination of the Voltage Holding Ratio (VHR)

Two glass plates coated with Comparative Polyamic Acid No. 2 (same procedure as used in EXAMPLE 19) were irradiated perpendicularly during 4 minutes with linearly polarised UV light. From both plates a cell of 10 μm spacing was built such that the illuminated surfaces were facing each other and the previous polarisation directions of illumination were parallel. This cell was then maintained at 120° C. under high vacuum for 14 h and thereafter filled with TFT liquid crystal mixture MLC6610 from Merck in vacuum at room temperature. Between crossed polarisers a uniformly oriented liquid crystal layer was observed. Prior to testing the voltage holding ratio (VHR) the cell was first subjected to ageing for 50 h at 120° C. The voltage decay V (at T=20 ms) of a voltage surge of 64 μs with $V_0$ (V at t=0)=0.2V was then measured over a period of T=20 ms. The voltage holding ratio then determined, given by VHR=$V_{rms}$(t=T)/$V_0$, was 99% at room temperature and 94% at 80° C.

EXAMPLE 27

Comparative Example C for the Production of an Orientation Layer having a Defined Tilt Angle Two glass plates coated with Comparative Polyamic Acid 3 (same procedure as used in EXAMPLE 19) were irradiated with linearly polarised UV light (50 mJ/cm$^2$), the direction of incidence of the light being inclined by 20° to 40° relative to the plate normal. The direction of polarisation of the light was kept in the plane defined by the direction of incidence of the light and the plate normal. From both plates a cell of 20 μm spacing was built such that the illuminated surfaces were facing each other and the previous polarisation directions of illumination were parallel. The cell was then filled with liquid crystal mixture MLC6609 from Merck in the isotropic phase at 100° C. The cell was then gradually cooled to room temperature at a rate ranging from 0.1° C./min to 2° C./min. Between crossed polarisers a uniformly oriented liquid crystal layer was observed. The tilt angle of this parallel cell, by crystal rotation method, was 88.5°.

EXAMPLE 28

Comparative Example C for the Determination of the Voltage Holding Ratio (VHR)

Two glass plates coated with Comparative Polyamic Acid 3 (same procedure as used in EXAMPLE 19) were irradiated perpendicularly during 4 minutes with linearly polarised UV light. From both plates a cell of 10 μm spacing was built such that the illuminated surfaces were facing each other and the previous polarisation directions of illumination were parallel. This cell was then maintained at 120° C. under high vacuum for 14 h and thereafter filled with TFT liquid crystal mixture MLC6610 from Merck in vacuum at room temperature. Between crossed polarisers a uniformly oriented liquid crystal layer was observed. Prior to testing the voltage holding ratio (VHR) the cell was first subjected to ageing for 50 h at 120° C. The voltage decay V (at T=20 ms) of a voltage surge of 64 μs with $V_0$ (V at t=0)=0.2V was then measured over a period of T=20 ms. The voltage holding ratio then determined, given by VHR=$V_{rms}$(t=T)/$V_0$, was 82% at room temperature and 56% at 80° C.

EXAMPLE 29

Comparative Example C for the Determination of the Tilt Angle's Photo-Stability

An orientation layer having a defined angle of tilt in accordance with Example 27 has been subjected to photo-stability experiments using a HANAU SUNTESTER apparatus. The light impact on the sample had a cut-off at 400 nm and an irradiance of 60 mW/cm$^2$. The above angle of tilt was stable over a time period of 800 h.

EXAMPLE 30

Comparative Example D for the Production of an Orientation Layer having a Defined Tilt Angle Two glass plates coated with Comparative Polyamic Acid No. 4 (same procedure as used in EXAMPLE 19) were irradiated with linearly polarised UV light (30 mJ/cm$^2$), the direction of incidence of the light being inclined by 20° to 40° relative to the plate normal. The direction of polarisation of the light was kept in the plane defined by the direction of incidence of the light and the plate normal. From both plates a cell of 20 μm spacing was built such that the illuminated surfaces were facing each other and the previous polarisation directions of illumination were parallel. The cell was then filled with liquid crystal mixture MLC6609 from Merck in the isotropic phase at 100° C. The cell was then gradually cooled to room temperature at a rate ranging from 0.1° C./min to 2° C./min. Between crossed polarisers a uniformly oriented liquid crystal layer was observed. The tilt angle of this parallel cell, by crystal rotation method, was 0° C.

EXAMPLE 31

Comparative Example D for the Determination of the Voltage Holding Ratio (VHR)

Two glass plates coated in accordance with Example 30 were irradiated perpendicularly during 4 minutes with linearly polarised UV light. From both plates a cell of 10 μm spacing was built such that the illuminated surfaces were facing each other and the previous polarisation directions of illumination were parallel. This cell was then maintained at 120° C. under high vacuum for 14 h and thereafter filled with TFT liquid crystal mixture MLC6610 from Merck in vacuum at room temperature. Between crossed polarisers a uniformly oriented liquid crystal layer was observed. Prior to testing the voltage holding ratio (VHR) the cell was first subjected to ageing for 50 h at 120° C. The voltage decay V (at T=20 ms) of a voltage surge of 64 μs with $V_0$ (V at t=0)=0.2V was then measured over a period of T=20 ms. The voltage holding ratio then determined, given by $VHR=V_{rms}(t=T)/V_0$, was 99.5% at room temperature and 93.9% at 80° C.

The invention claimed is:
1. Diamine compound represented by one of the general formulae (Ia) and (Ib):

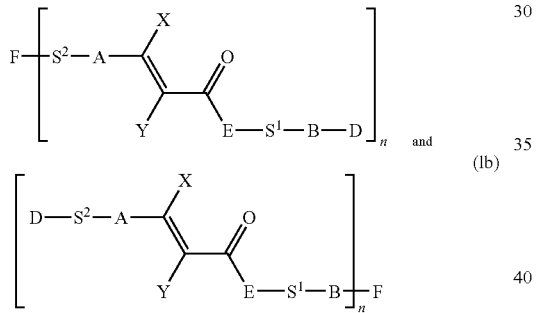

wherein:
A, B each independently represents a substituted or unsubstituted pyrimidine-diyl, pyridine-diyl, thiophenylene, furanylene, phenanthrylene, naphthylene, biphenylene or phenylene,
D represents a hydrogen atom, a halogen atom, a polar group which is nitro, cyano, carboxy, —$CF_3$, —Si$(CH_3)_3$, —Si$(CH_3)_2$—O—Si$(CH_3)_3$, a silane group, a siloxane group, or a cyclic, straight-chain or branched alkyl residue having from 1 to 40 carbon atoms, which is unsubstituted, mono-substituted or poly-substituted by cyano, fluorine, chlorine, an alicyclic group and/or by $CH_2$=CW-, or $CH_2$=CW-(CO)$_v$O—, wherein:
W represents H or —$CH_3$ and
v is 0 or 1, and
wherein one or more non-adjacent —$CH_2$— groups may independently be replaced by a group $G^2$, wherein:
$G^2$ represents a group selected from —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, or —Si$(CH_3)_2$—O—Si$(CH_3)_2$—, wherein $R^1$ represents a hydrogen atom or lower alkyl; and E represents an oxygen atom, a sulfur atom, —C$(R^2)R^3$— or —$NR^4$—, wherein:
$R^2$, $R^3$ is independently hydrogen or a cyclic, straight-chain or branched alkyl residue which is unsubstituted, mono-substituted by cyano, fluorine or chlorine, or poly-substituted by fluorine and/or chlorine, having from 1 to 24 carbon atoms, wherein one or more non-adjacent —$CH_2$— groups may independently be replaced by a group $G^3$, wherein:
$G^3$ represents a group selected from —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C—, —O—CO—O—, —Si$(CH_3)_2$— and —Si$(CH_3)_2$—O—Si$(CH_3)_2$—, wherein $R^1$ is defined as above;
with the proviso that at least one of $R^2$ and $R^3$ is not hydrogen; and
$R^4$ represents a hydrogen atom or lower alkyl; and
$S^1$, $S^2$ each independently represents a single bond or a straight-chain or branched alkylene group which is unsubstituted, mono or poly-substituted by a cyano group and/or by halogen atoms, having from 1 to 24 carbon atoms, wherein one or more —$CH_2$— groups may independently be replaced by a group represented by the general formula (II):

wherein:
$C^1$, $C^2$ each independently represents an optionally-substituted, non-aromatic or aromatic, carbocyclic or heterocyclic group; and
$Z^1$, $Z^2$ each independently represents a group selected from —CH(OH)—, —O—, —CO—, —$CH_2$(CO)—, —SO—, —$CH_2$(SO)—, —$SO_2$—, —$CH_2(SO_2)$—, —COO—, —OCO—, —$COCF_2$—, —$CF_2CO$—, —S—CO—, —CO—S—, —SOO—, —OSO—, —SOS—, —$CH_2$—$CH_2$—, —$OCH_2$—, —$CH_2O$—, —CH=CH—, —C≡C—, —CH=CH—COO—, —OCO—CH=CH—, —CH=N—, —C($CH_3$)=N—, —N=N—, —O—CO—O—, or a single bond; and
$a^1$, $a^2$ each independently represents an integer from 0 to 3, whereby $a^1+a^2 \leq 4$; and F represents an optionally substituted aliphatic, aromatic or alicyclic diamino group having from 1 to 40 carbon atoms selected from formula (III):

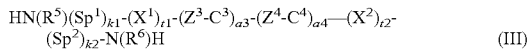

wherein:
$Sp^1$, $Sp^2$ each independently represents an optionally-substituted straight-chain or branched alkylene group having from 1 to 20 carbon atoms, in which one or more non-adjacent C-atoms may be replaced by a heteroatom and/or by a group selected from —O—, —CO—, —CO—O—, —O—CO—, —$NR^1$—, —$NR^1$—CO—, —CO—$NR^1$—, —$NR^1$—CO—O—, —O—CO—$NR^1$—, —$NR^1$—CO—$NR^1$—, —O—CO—O—, or —Si$(CH_3)_2$—O—Si$(CH_3)_2$—, wherein $R^1$ is defined as above; and in which one or more carbon-carbon single bonds may be replaced by a carbon-carbon double or by a carbon-carbon triple bond; and
$R^5$, $R^6$ each independently represents a hydrogen atom or lower alkyl; and $k^1$, $k^2$ each independently is an integer having a value of 0 or 1; and $X^1$, $X^2$ each independently represents a group selected from —O—, —S—, —NH—, —N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —CH$_2$—CH$_2$—, —OCH$_2$—, —CH$_2$O—, —CH=CH—, or —C≡C— or a single bond; and $t^1$, $t^2$ each independently is an integer having of a value of 0 or 1; and $C^3$, $C^4$ each independently represents an optionally-substituted non-aromatic, aromatic, carbocyclic or heterocyclic group; and $Z^3$ represents a group selected from —CH(OH)—, —CH(CH$_3$)—, —C(CH$_3$)$_2$—, —CO—, —CH$_2$(CO)—, —SO—, —CH$_2$(SO)—, —SO$_2$—, —CH$_2$(SO$_2$)—, —COO—, —OCO—, —COCF$_2$—, —CF$_2$CO—, —S—CO—, —CO—S—, —SOO—, —OSO—, —SOS—, —CH$_2$—CH$_2$—, —OCH$_2$—, —CH$_2$O—, —CH=CH—, —C≡C—, —CH=CH—COO—, —OCO—CH=CH—, —CH=N—, —C(CH$_3$)=N—, —N=N—, —O—CO—O—, or a single bond; and $Z^4$ has one of the meanings of $Z^3$ or represents an Optionally-substituted straight-chain or branched alkylene group having from 1 to 20 carbon atoms, in which one or more —CH$_2$— groups may be replaced by a heteroatom and/or by a group $Z^3$ as defined above and/or one or more carbon-carbon single bonds may be replaced by a carbon-carbon double bond or a carbon-carbon triple bond; and $a^3$, $a^4$ are independently integers from 0 to 3, whereby $$a^3+a^4 \leq 4;$$

and wherein:

F is linked to group $S^2$ in formula (Ia) or to group B in formula (Ib) via group $Sp^1$ and/or group $C^3$ and/or group $Z^4$ and/or group $C^4$ and/or group $Sp^2$, with the proviso that at least one of $t^1$, $t^2$, $a^3$ and $a^4$ is not equal to zero, and X, Y each independently represent hydrogen, fluorine, chlorine, cyano, alkyl, optionally substituted by fluorine, having from 1 to 12 carbon atoms, in which optionally one or more non-adjacent —CH$_2$— groups are replaced by a group $Z^1$, and n is 1, 2, 3, or 4.

2. Diamine compound according to claim 1, wherein the carbocyclic or heterocyclic aromatic group in A and B is independently selected from the group of substituted or unsubstituted phenanthrylene, biphenylene, naphthylene, or phenylene, in particular from substituted or preferably unsubstituted 1,2-, 1,3-, or 1,4-phenylene, 2,7-phenanthrylene, 4,4'-biphenylene, 2,6-naphthylene, or 2,7-naphthylene.

3. Diamine compound according to claim 1, wherein the carbocyclic or heterocyclic aromatic group in A and B is independently substituted by an acryloyloxy, alkoxy, alkylcarbonyloxy, alkyloxycarbonyloxy, alkyloxocarbonyloxy, methacryloyloxy, vinyl, vinyloxy or allyloxy group, having from 1 to 20 carbon atoms, preferentially having from 1 to 10 carbon atoms.

4. Diamine compound according to claim 1, wherein the carbocyclic or heterocyclic aromatic group in A and B is independently substituted by a cyclic, straight-chain or branched alkyl residue having from 1 to 20 carbon atoms, preferentially 1-10 carbon atoms, which is unsubstituted, mono- or poly-substituted by fluorine and/or chlorine.

5. Diamine compound according to claim 1, wherein B is selected from phenanthrylene, biphenylene, naphthylene, or phenylene, in particular from 1,2-, 1,3-, or 1,4 phenylene, 2,7-phenanthrylene, 4,4'-biphenylene, 2,6-naphthylene, or 2,7-naphthylene.

6. Diamine compound according to claim 1, wherein B is 1,4 phenylene.

7. Diamine compound according to claim 1, wherein B is 1,4-phenylene, E is —O— and $S^1$ is a single bond.

8. Diamine compound according to claim 1, wherein D represents a straight-chain or branched alkyl residue having from 1 to 30 carbon atoms, preferentially from 1 to 16 carbon atoms, which is unsubstituted, mono-substituted by fluorine, chlorine, acryloxy, methacryloxy or poly-substituted by fluorine and/or chlorine.

9. Diamine compound according to claim 1, wherein $G^2$ represents a group selected from —O—, —CO—, —CO—O—, —O—CO—, —NR$^1$—CO—O—, —O—CO—NR$^1$—, —CH=CH—, —C≡C—, or —Si(CH$_3$)$_2$—O—Si(CH$_3$)$_2$—.

10. Diamine compound according to claim 1, wherein D represents a straight-chain or branched alkyl residue having from 1 to 20 carbon atoms represented by the general formula (IV):

$$P^1\text{-}Sp^3\text{-}X^3\text{—} \qquad (IV)$$

wherein:

$P^1$ represents hydrogen, a halogen atom, a silane group, CH$_2$=CW-, or CH$_2$=CW-(CO)$_v$O—, wherein:

W represents H or —CH$_3$; and v is 0 or 1; and $Sp^3$ represents a straight-chain or branched alkyl, alkoxy, alkoxycarbonyl, alkylcarbonyl or alkylcarbonyloxy group having from 1 to 30 carbon atoms, preferentially having from 1 to 12 carbon atoms, which is mono- or poly-substituted by fluorine and/or chlorine and wherein optionally one or more —CH$_2$— groups may independently be replaced by one or more groups selected from —O—, —CO—, —CO—O—, —O—CO—, —NR$^1$—CO—, —CO—NR$^1$—, —NR$^1$—CO—O—, —O—CO—NR$^1$—, —CH=CH—, —C≡C— and —Si(CH$_3$)$_2$—O—Si(CH$_3$)$_2$—, wherein:

$R^1$ is as defined above;

with the proviso that oxygen atoms are not directly linked to each other; and $X^3$ has one of the meanings of $X^1$ given above.

11. Diamine compound according to claim 10, wherein $Sp^3$ is selected from methyl, ethyl, propyl, butyl, pentyl, hexyl, heptyl, octyl, nonyl, decyl, undecyl, dodecyl, methoxy, ethoxy, n-propoxy, isopropoxy, butoxy, pentyloxy, hexyloxy, heptyloxy, octyloxy, nonyloxy, decyloxy, undecyloxy, dodecyloxy, methoxycarbonyl, ethoxycarbonyl, propoxycarbonyl, butoxycarbonyl, pentyloxycarbonyl, hexyloxycarbonyl, octyloxycarbonyl, nonyloxycarbonyl, decyloxycarbonyl, undecyloxycarbonyl, dodecyloxycarbonyl, acetyl, propionyl, butyryl, valeryl, hexanoyl, heptanoyl, octanoyl, nonanoyl, decanoyl, undecanoyl, dodecanoyl, terdecanoyl, acetoxy, propionyloxy, butyryloxy, valeryloxy, hexanoyloxy, heptanoyloxy, octanoyloxy, nonanoyloxy, decanoyloxy, undecanoyloxy, dodecanoyloxy, terdecanoyloxy; which may be mono- or poly-substituted by fluorine.

12. Diamine compound according to claim 10, wherein $P^1$ represents hydrogen or fluorine.

13. Diamine compound according to claim 1, wherein E represents an oxygen atom, or a —NH— group, preferentially E represents an oxygen atom.

14. Diamine compound according to claim 1, wherein $C^1$ and $C^2$ are connected to each other at opposite positions via the bridging groups $Z^1$ and $Z^2$.

15. Diamine compound according to claim 1, wherein $C^1$, $C^2$ are selected from:

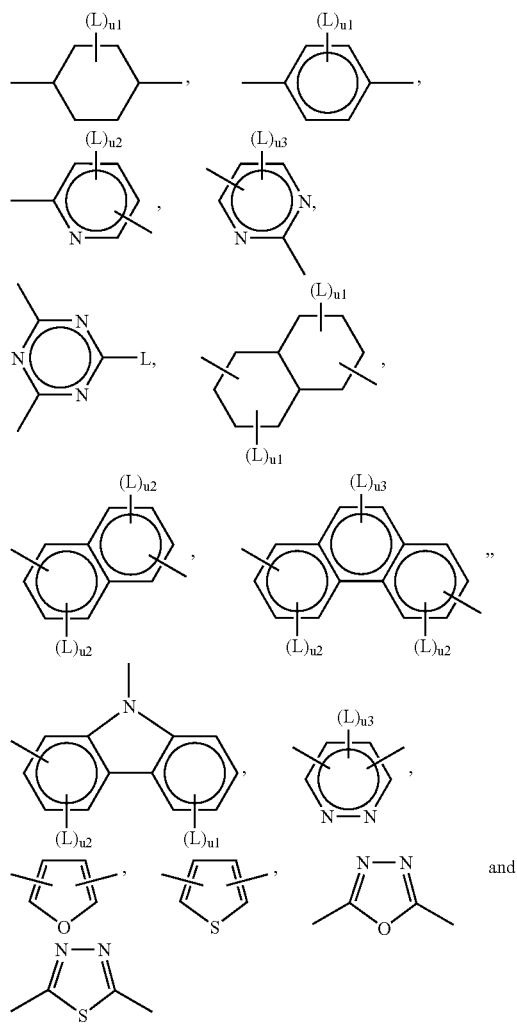

wherein:
— denotes the connecting bonds of $C^1$ and $C^2$ to the adjacent groups; and L is —$CH_3$, —$COCH_3$, nitro, cyano, halogen, $CH_2$=CW— or $H_2$=CW-(CO)$_v$O—; wherein:
W represents H or —$CH_3$;
v is 0 or 1;
$u^1$ is an integer from 0 to 4;
$u^2$ is an integer from 0 to 3;
$u^3$ is an integer from 0 to 2; and
$Z^1$, $Z^2$ each independently represents —O—, —CO—, —COO—, —OCO—, —COCF$_2$—, —CF$_2$CO—, —CH$_2$—CH$_2$—, —OCH$_2$—, —CH$_2$O—, —CH=CH—, —C≡C—, —CH=CH—COO—, —OCO—CH=CH— or a single bond;

with the proviso that heteroatoms are not directly linked to each other, and $a^1$, $a^2$ each independently represents an integer from 0 to 3, whereby $$a^1 + a^2 \leq 4.$$

16. Diamine compound according to claim 1, wherein $S^1$, $S^2$ each independently represents a single bond or a straight-chain or branched alkylene group having from 1 to 14 carbon atoms, wherein one or more —$CH_2$— groups may independently be replaced by a group represented by formula (II), wherein:

$C^1$, $C^2$ each independently represents a 1,4-phenylene, 1,4-cyclohexylene or a 4,4'-biphenylene group; and $Z^1$, $Z^2$ each independently represents —COO—, —OCO—, —CH$_2$—CH$_2$—, —OCH$_2$—, —CH$_2$O—, —CH=CH—, —C≡C—, —CH=CH—COO—, —OCO—CH=CH— or a single bond; and $a^1$, $a^2$ are independently 0 or 1.

17. Diamine compound according to claim 1, wherein $C^3$ and $C^4$ are connected to each other at the opposite positions via the bridging groups $Z^3$ and $Z^4$.

18. Diamine compound according to claim 1, wherein

F represents an optionally substituted aliphatic, aromatic or alicyclic diamino group having from 1 to 40 carbon atoms;

$k^1$, $k^2$ are 0 or 1, $t^1$, $t^2$ are 0, and $R^5$, $R^6$ are identical and represent a hydrogen atom, a methyl, an ethyl or an isopropyl group; and $C^3$, $C^4$ independently from each other have one of the meanings of $C^1$; and $Z^3$ represents a group selected from —CH(OH)—, —CH(CH$_3$)—, —C(CH$_3$)$_2$—, —CO—, —COO—, —COCF$_2$—, —CF$_2$CO— or a single bond; and $Z^4$ has one of the meanings of $Z^3$ or represents an optionally-substituted straight-chain or branched alkylene group having from 1 to 16 carbon atoms, in which one or more —$CH_2$— groups may be replaced by an oxygen atom and/or one or more carbon-carbon single bonds may be replaced by a carbon-carbon double or a carbon-carbon triple bond; and $a^3$, $a^4$ each independently represents an integer from 0 to 2, whereby $a^3 + a^4 \leq 3$.

19. Diamine compound according to claim 1, wherein

F is selected from or based on one of the structures selected from the group: aniline, p-phenylenediamine, m-phenylenediamine, benzidine, diaminofluorene or their derivatives; 4-amino-2,3,5,6-tetrafluorobenzoic acid, 4-amino-3,5-diiodobenzoic acid, 3,4-diaminobenzoic acid, 4-amino-3-methylbenzoic acid, 4-amino-2-chlorobenzoic acid, 4-aminosalicylic acid, 4-aminobenzoic acid, 4-aminophthalic acid 1-(4-aminophenyl)ethanol, 4-aminobenzyl alcohol, 4-amino-3-methoxybenzoic acid, 4-aminophenyl ethyl carbinol, 4-amino-3-nitrobenzoic acid, 4-amino-3,5-dinitrobenzoic acid, 4-amino-3,5-dichlorobenzoic acid, 4-amino-3-hydroxybenzoic acid, 4-aminobenzyl alcohol hydrochloride, 4-aminobenzoic acid hydrochloride, pararosaniline base, 4-amino-5-chloro-2-methoxybenzoic acid, 4-(hexafluoro-2-hydroxyisopropyl)aniline, piperazine-p-amino benzoate, 4-amino-3,5-dibromobenzoic acid, isonicotinic acid hydrazide p-aminosalicylate salt, 4-amino-3,5-diiodosalicylic acid, 4-amino-2-methoxybenzoic acid, 2-[2-(4-aminophenyl)-2-hydroxy-1-(hydroxymethyl)ethyl]isoindoline-1,3-dione, 4-amino-2-nitrobenzoic acid, 2,4-diaminobenzoic acid, p-aminobenzoic acid, [3,5-3h]-4-amino-2-methoxybenzoic acid, L-(+)-threo-2-amino-1-(4-aminophenyl)-1,3-propanediol, L-(+)-threo-2-(n,n-dimethylamino)-1-(4-aminophenyl)-1,3-propanediol, ethyl 2-(4-aminophenyl)-3,3,3-trifluoro-2-hydroxypropanoate, ethyl 2-(4-amino-3-methylphenyl)-3,3,3-trifluoro-2-hydroxypropanoate, ethyl 2-(4-amino-3-methoxyphenyl)-3,3,3-trifluoro-2-hydroxypropanoate, 3,4-diaminobenzyl alcohol dihydrochloride, 4-aminonaphthalene-1,8-dicarboxylic acid, 4-amino-3-chloro-5-methylbenzoic acid, 4-amino-2,6-dimethylbenzoic acid, 4-amino-3-fluorobenzoic acid, 4-amino-5-bromo-2-methoxybenzenecarboxylic acid, 2,7-diaminofluorene, 4,4'-diaminooctafluorobiphenyl, 3,3'-diaminobenzidine, 3,3',5,5'-tetramethylbenzidine, 3,3'-dimethoxybenzidine, o-tolidine, 3,3'-dinitrobenzidine, 2-nitrobenzidine, 3,3'-dihydroxybenzidine, o-tolidine sulfone, benzidine, 3,3'-dichlorobenzidine, 2,2',5,5'-tetrachlorobenzidine, benzidine-3,3'-dicarboxylic acid, 4,4'-diamino-1,1'-binaphthyl, 4,4'-diaminodiphenyl-3,3'-diglycolic acid, dihydroethidium, o-dianisidine, 2,2'-dichloro-5,5'-dimethoxybenzidine, 3-methoxybenzidine, 3,3'-dichlorobenzidine (diphenyl-d6), 2,7-diamino-9-fluorenone, 3,5,3',5'-tetrabromo-biphenyl-4,4'-diamine, 2,2'-bis(trifluoromethyl)benzidine, 2,2'-dichloro[1,1'-biphenyl]-4,4'-diamine, 3,9-diamino-1,11-dimethyl-5,7-dihydrodibenzo(a,c)cyclohepten-6-one, 3,3'-bis(trifluoromethyl)benzidine, dibenzo(1,2)dithiine-3,8-diamine, 3,3'-tolidine-5-sulfonic acid, 3,3'-dichlorobenzidine-d6, tetramethylbenzidine, 3,3'-diaminobenzophenone, 3,3'-diaminodiphenylmethane, 4,4-bis-(3-amino-4-hydroxyphenyl)-valeric acid, 2,2-bis(3-amino-4-hydroxyphenyl)hexafluoropropane, 2,2-bis(3-amino-4-methylphenyl)hexafluoropropane, tetrabromo methylenedianiline, 2,7-diamino-9-fluorenone, 2,2-bis(3-aminophenyl)hexafluoropropane, bis-(3-amino-4-chloro-phenyl)-methanone, bis-(3-amino-4-dimethylaminophenyl)-methanone, 3-[3-amino-5-(trifluoromethyl)benzyl]-5-(trifluoromethyl)aniline, 1,5-diaminonaphthalene or their derivatives.

20. Diamine compound according to claim 1, wherein n is 1, 2 or 3, preferably 1 or 2.

21. Diamine compound according to claim 1, wherein n is 1.

22. Diamine compound according to claim 1, wherein $a^1+a^2 \leq 3$, preferably $a^1+a^2 \leq 2$ or $a^1+a^2 \leq 1$.

23. Diamine compound according to claim 1, comprising a photo-reactive group that can be photo-isomerized and/or photo-dimerized on exposure to visible light, UV light or laser light.

24. Polymer or oligomer from the class of polyamic acids, polyamic acid esters or polyimides, or mixtures thereof obtained by or obtainable by the reaction of at least one diamine compound according to claim 1 and optionally of one or more additional other diamines, with one or more tetracarboxylic acid anhydrides of the general formula (V):

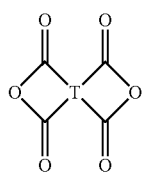

(V)

wherein:
T represents a tetravalent organic radical.

25. Polymer or oligomer according to claim 24, wherein the tetravalent organic radical T is derived from an aliphatic, alicyclic or aromatic tetracarboxylic acid dianhydride.

26. Polymer or oligomer according to claim 24, wherein T is selected from the group: 1,1,4,4-butanetetracarboxylic acid dianhydride,
ethylenemaleic acid dianhydride, 1,2,3,4-cyclobutanetetracarboxylic acid dianhydride, 1,2,3,4-cyclopentanetetracarboxylic acid dianhydride, 2,3,5-tricarboxycyclopentylacetic acid dianhydride, 3,5,6-tricarboxynorbornylacetic acid dianhydride, 2,3,4,5-tetrahydrofurantetracarboxylic acid dianhydride, rel-[1S,5R,6R]-3-oxabicyclo[3.2.1]octane-2,4-dione-6-spiro-3'-(tetrahydrofuran2',5'-dione), 4-(2,5-dioxotetrahydrofuran-3-yl)tetrahydronaphthalene-1,2-dicarboxylicacid dianhydride, 5-(2,5-dioxotetrahydrofuran-3-yl)-3-methyl-3-cyclohexene-1,2-dicarboxylic-acid dianhydride, bicyclo[2.2.2]oct-7-ene-2,3,5,6-tetracarboxylic acid dianhydride, bicyclo[2.2.2]octane-2,3,5,6-tetracarboxylic acid dianhydride, 1,8-dimethylbicycl[2.2.2]oct-7-ene-2,3,5,6-tetracarboxylic acid dianhydride, pyromellitic acid dianhydride, 3,3',4,4'-benzophenonetetracarboxylic acid dianhydride, 4,4'-oxydiphthalic acid dianhydride, 3,3',4,4'-diphenylsulfonetetracarboxylic acid dianhydride, 1,4,5,8-naphthalenetetracarboxylic acid dianhydride, 2,3,6,7-naphthalenetetracarboxylic acid dianhydride, 3,3',4,4'-dimethyldiphenylsilanetetracarboxylic acid dianhydride, 3,3',4,4'-tetraphenylsilanetetracarboxylic acid dianhydride, 1,2,3,4-furantetracarboxylic acid dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-biphenyltetracarboxylic acid dianhydride, ethylene glycol bis(trimellitic acid) dianhydride, 4,4'-(1,4-phenylene)bis(phthalic acid) dianhydride, 4,4'-(1,3-phenylene)bis(phthalic acid) dianhydride, 4,4'-(hexafluoroisopropylidene)diphthalic acid dianhydride, 4,4'-oxydi(1,4-phenylene)bis(phthalic acid) dianhydride, and 4,4'-methylenedi(1,4-phenylene)bis(phthalic acid) dianhydride.

27. Polymer or oligomer according to claim 24, wherein the one or more additional other diamine is selected from the group: ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10-decylenediamine, 1,11-undecylenediamine, 1,12-dodecylenediamine, α,α'-diamino-m-xylene, α,α'-diamino-p-xylene, (5-amino-2,2,4-trimethylcyclopentyl)methylamine, 1,2-diaminocyclohexane, 4,4'-diaminodicyclohexylmethane, 1,3-bis(methylamino)cyclohexane, 4,9-dioxadodecane-1,12-diamine, 3,5-diaminobenzoic acid methyl ester, 3,5-diaminobenzoic acid hexyl ester, 3,5-diaminobenzoic acid dodecyl ester, 3,5-diaminobenzoic acid isopropyl ester, 4,4'-methylenedianiline, 4,4-ethylenedianiline, 4,4'-diamino-3,3'-dimethyldiphenylmethane, 3,3',5,5'-tetramethylbenzidine, 4,4'-diaminodiphenyl sulfone, 4,4'-diaminodiphenyl ether, 1,5-diaminonaphthalene, 3,3'-dimethyl-4,4'-diaminobiphenyl, 3,4-diaminodiphenyl ether, 3,3'-diaminobenzophenone, 4,4'-diaminobenzophenone, 4,4'-diamino-2,2'-dimethylbibenzyl, bis[4-(4-aminophenoxy)phenyl] sulfone, 1,4-bis(4-aminophenoxy)benzene, 1,3-bis(4-aminophenoxy)benzene, 1,3-bis(3-aminophenoxy)benzene, 2,7-diaminofluorene, 9,9-bis(4-aminophenyl)

fluorene, 4,4'-methylenebis(2-chloroaniline), 4,4'-bis(4-aminophenoxy)biphenyl, 2,2',5,5'-tetrachloro-4,4'-diaminobiphenyl, 2,2'-dichloro-4,4'-diamino-5,5'-dimethoxybiphenyl, 3,3'-dimethoxy-4,4'-diaminobiphenyl, 4,4'-(1,4-phenyleneisopropylidene)bisaniline, 4,4'-(1,3-phenyleneisopropylidene)bisaniline, 2,2-bis[4-(4-aminophenoxy)phenyl]propane, 2,2-bis[3-(4-aminophenoxy)phenyl] hexafluoropropane, 2,2-bis[3-amino-4-methylphenyl] hexafluoropropane, 2,2-bis(4-aminophenyl) hexafluoropropane, 2,2-bis[4-(4-amino-2-trifluoromethylphenoxy)phenyl]hexafluoropropane, 4,4'-diamino-2,2'-bis(trifluoromethyl)biphenyl, and 4,4'-bis[(4-amino-2-trifluoromethyl)phenoxy]-2,3,5,6,2',3',5',6'-octafluorobiphenyl.

28. Polymer or oligomer according to claim 24, comprising as side-chains a photo-reactive group that can be photo-isomerized and/or photo-dimerized on exposure to visible light, UV light or laser light.

29. Polymer or oligomer according to claim 28, wherein at least 30%, preferably at least 75% of the repeating units include a side chain with a photo-reactive group.

30. Polymer or oligomer according to claim 28, wherein the photo-reactive groups are able to undergo photo-cyclization, in particular [2+2]-photo-cyclisation.

31. Polymer or oligomer according to claim 24, wherein the polymer or oligomer is a polymer gel or a polymer network, or an oligomer gel or an oligomer network, respectively.

32. Polymer or oligomer according to claim 24, with an intrinsic viscosity in the range of 0.05 to 10 dL/g, preferably in the range of 0.05 to 5 dL/g.

33. Polymer or oligomer according to claim 24, containing from 2 to 2000 repeating units, especially from 3 to 200 repeating units.

34. Polymer or oligomer according to claim 24, in the form of a homopolymer or of a copolymer, preferably of a statistical copolymer.

35. Polymer or oligomer according to claim 24, wherein the polymer or oligomer is cross-linkable or cross-linked.

36. Polymer or oligomer according to claim 24, additionally comprising additives which are silane-containing compounds, one or more photo-sensitizers and/or one or more photo-radical generators and/or one or more cationic photo-initiators and/or cross-linking agents, preferably epoxy-containing cross-linking agents, most preferably selected from the group:

4,4'-methylene-bis-(N,N-diglycidylaniline), trimethylolpropane triglycidyl ether, benzene-1,2,4,5-tetracarboxylic acid 1,2,4,5-N,N'-diglycidyldiimide, polyethylene glycol diglycidyl ether, N,N-diglycidylcyclohexylamine.

37. Method for the preparation of a polymer or oligomer according to claim 24, wherein in a polycondensation reaction the at least one diamine compound is reacted with one or more tetracarboxylic acid anhydrides of the general formula (V), optionally in the presence of one or more additional other diamines.

38. Method according to claim 37, wherein a poly-condensation reaction for the preparation of the polyamic acids is carried out in solution in a polar aprotic organic solvent, preferably selected from γ-butyrolactone, N,N-dimethylacetamide, N-methylpyrrolidone or, N,N-dimethylformamide.

39. Method according to claim 37, wherein subsequent to the poly-condensation cyclisation with removal of water is carried out thermally under formation of a polyimide.

40. Method according to claim 39, wherein imidisation is carried out prior or after the application of the polymer or oligomer to a support.

41. Polymer or oligomer layer, in particular orientation layer, comprising at least one polymer or oligomer according to claim 24.

42. Method for the preparation of a polymer layer or oligomer layer according to claim 37, wherein one or more of the polymer or oligomer is applied to a support, preferably from a solution of the polymer or oligomer material and subsequent evaporation of the solvent, and wherein, after any imidisation step which may be necessary, the polymer or oligomer or polymer mixture or oligomer mixture is cross-linked by irradiation with linearly polarized light.

43. Method according to claim 42, wherein the direction of orientation and the tilt angle within the polymer layer or oligomer layer is varied by controlling the direction of the irradiation of the linearly polarized light, and/or wherein by selectively irradiating specific regions of the polymer layer or oligomer layer specific regions of the layer are aligned.

44. Method of forming an orientation layer for liquid crystals, comprising orienting the polymer layer or oligomer layer according to claim 41 by irradiation to form an orientation layer for liquid crystals.

45. Method of orienting liquid crystals, comprising inducting vertical alignment of adjacent liquid crystalline layers, in particular for operating a cell in MVA mode, with the polymer layer or oligomer layer according to claim 41.

46. Optical and electro-optical unstructured or structured constructional elements, preferably liquid crystal display cells, multi-layer and hybrid layer elements, comprising at least one polymer layer or oligomer layer according to claim 41.

* * * * *